US007960361B2

(12) United States Patent
Debinski et al.

(10) Patent No.: US 7,960,361 B2
(45) Date of Patent: Jun. 14, 2011

(54) NUCLEIC ACID CANCER IMMUNOTHERAPY

(75) Inventors: Waldemar Debinski, Winston-Salem, NC (US); Neil Christensen, Harrisburg, PA (US); Akiva Mintz, Brooklyn, NY (US)

(73) Assignee: The Penn State Research Foundation, University Park, PA (US)

( * ) Notice: Subject to any disclaimer, the term of this patent is extended or adjusted under 35 U.S.C. 154(b) by 293 days.

(21) Appl. No.: 12/020,391

(22) Filed: Jan. 25, 2008

(65) Prior Publication Data

US 2008/0166374 A1     Jul. 10, 2008

Related U.S. Application Data

(60) Division of application No. 10/104,408, filed on Mar. 22, 2002, now Pat. No. 7,338,929, which is a continuation-in-part of application No. 09/780,926, filed on Feb. 8, 2001, now abandoned.

(60) Provisional application No. 60/181,000, filed on Feb. 8, 2000.

(51) Int. Cl.
   *A61K 48/00*     (2006.01)
(52) U.S. Cl. .................................. 514/44 R; 536/23.52
(58) Field of Classification Search .................. None
   See application file for complete search history.

(56) References Cited

U.S. PATENT DOCUMENTS

| 5,614,191 | A |   | 3/1997 | Puri et al. |
| 5,710,023 | A |   | 1/1998 | Collins et al. |
| 5,827,703 | A |   | 10/1998 | Debs et al. |
| 5,855,866 | A |   | 1/1999 | Thorpe et al. |
| 6,248,714 | B1 | * | 6/2001 | Collins et al. ............... 514/2 |
| 7,268,120 | B1 | * | 9/2007 | Horton et al. ............ 514/44 R |
| 2003/0157691 | A1 |   | 8/2003 | Qin et al. |

FOREIGN PATENT DOCUMENTS

| WO | WO 97/47741    | * | 12/1997 |
| WO | WO 01/58479    |   | 8/2001 |
| WO | WO 02/097114 A2 |   | 12/2002 |
| WO | WO 03/079757 A2 |   | 10/2003 |

OTHER PUBLICATIONS

Granziero et al. Eur. J. Immunol. 1999, 29:1127-1138.*
Byers, T., CA Journal, vol. 49, No. 6, Nov./Dec. 1999.*
Bellone et al. (Immunology Today, 1999, 20:457-462.*
Debinski et al., "Human Gliomas Cells Overexpress Receptors for Interleukin 13 and Are Extremely Sensitive to a Novel Chimeric Protein Composed of Interleukin 13 and Pseudomonas Exotoxin[1]," Clinical Cancer Research, 1: 1253-1258, 1995.
Debinski et al., "Novel Way to Increase Targeting Specificity to a Numan Glioblastoma-Associated Receptor for Interleukin 13," Int. J. Cancer, 76: 547-551, 1998.
Caput et al., "Cloning and Characterization of a Specific Interleukin (IL)-13 Binding Protein Structurally Related to the IL-5 Receptor α Chain," The Journal of Biological Chemistry, 271: 16921-16926, 1996.
Debinski, W., "Recombinant Cytotoxins Specific for Cancer Cells," Ann. NY Acad. Sci., 297-299, 1999.
Debinski et al., "Receptor for Interleukin 13 Is a Marker and Therapeutic Target for Human High-Grade Gliomast," Clinical Cancer Research, 5: 985-990, 1999.
Joshi et al., "Interleukin-13 Receptor α Chain: A Novel Tumor-associated Transmembrane Protein in Primary Explants of Human Malignant Gliomas," Cancer Research, 60: 1168-1172, 2000.
Barton et al. "Retroviral delivery of small interfering RNA into primary cells", PNAS, (2002), vol. 99, No. 23, pp. 14943-14945.
Noda et al. "Protection from Anti-TCR/CD3-induced Apoptosis in Immature Thymocytes by a Signal Through Thymic Shared Antigen-1/Stem Cell Antigen-2", J. Exp. Med., (1996), vol. 183, pp. 2355-2360.
Treister et al. "Expression of Ly-6, A Marker for Highly Malignant Murine Tumor Cells, is Regulated by Growth Conditions and Stress", Int. J. Cancer, (1998), vol. 77, pp. 306-313.
McManus et al. "Gene Silencing in Mammals by Small Interfering RNAs", Nature Reviews/Genetics, (2002), vol. 3, pp. 737-747.
Tuschl et al. "Small Interfering RNAs: A Revolutionary Tool for the Analysis of Gene Function and Gene Therapy", Molecular Interventions, (2002), vol. 2, No. 3, pp. 158-167.
Rubinson et al. "A lentivirus-based system to functionally silence genes in primary mammalian cells, stem cells and transgenic mice by RNA interference", Nature Genetics, (2003), vol. 33, pp. 401-406.
He et al. "Functional Characterization of Hepatoma-Specific Stem Cell Antigen-2", Molecular Carcinogenesis, (2004), vol. 40, pp. 90-103.
Banerjea et al. "Inhibition of HIV-1 by Lentiviral Vector-Transduced siRNAs in T Lymphocytes Differentiated in SCID-hu Mice and CD34 Progenitor Cell-Derived Macrophages", Molecular Therapy, (2003), vol. 8, No. 1, pp. 62-71.
Lee et al. "Inhibition of Human Immunodeficiency Virus Type 1 Replication in Primary Macrophages by Using Tat- or CCR5-Speclfic Small Interfering RNAs Expressed from a Lentivirus Vector", Journal of Virology, (2003), vol. 77, No. 22, pp. 11964-11972.
Lee et al. "Expression of small interfering RNAs targeted against HIV-1 rev transcripts in human cells", Nature Biotechnology, (2002), vol. 19, pp. 500-505.
Novina et al. "siRNA-directed inhibition of HIV-1 infection", Nature Medicine, (2002), vol. 8, No. 7, pp. 681-686.

(Continued)

*Primary Examiner* — Misook Yu
*Assistant Examiner* — Mark Halvorson
(74) *Attorney, Agent, or Firm* — Novak Druce + Quigg LLP

(57) ABSTRACT

A method for stimulating a immune response against IL-13Rα2 in a subject having or at risk for developing a disease having cells expressing IL-13Rα2 includes the steps of formulating the anti-cancer vaccine outside of the subject and administering the vaccine to the subject in an amount sufficient to stimulate an immune response against IL-13Rα2 in the subject. A composition for stimulating a immune response against IL-13Rα2 in a subject having or at risk for developing a disease having cells expressing IL-13Rα2 includes an isolated agent that can stimulate immune response against IL-13α2.

8 Claims, 9 Drawing Sheets

OTHER PUBLICATIONS

Coburn et al. "Potent and Specific Inhibition of Human Immunodeficiency Virus Type 1 Replication by RNA Interference", Journal of Virology, (2002), vol. 76, No. 18, pp. 9225-9231.

Boden et al. "Promoter choice affects the potency of HIV-1 specific RNA interference", Nucleic Acids Research, (2003), vol. 31, No. 17, pp. 5033-5038.

Pusch et al. "Nucleotide sequence homology requirements of HIV-1-specific short hairpin RNA", Nucleic Acids Research, (2003), vol. 31, No. 22, pp. 6444-6449.

Chang et al. "Lentiviral siRNAs targeting multiple highly conserved RNA sequences of human immunodeficiency virus type 1", Gene Therapy, (2005), vol. 12, pp. 1133-1144.

* cited by examiner

MAFVCLAIGCLYTFLISTTFGCTSSSDTEIKVNPPQDFEIVDPG
YLGYLYLQWQPPLSLDHFKECTVEYELKYRNIGSETWKTIIT
KNLHYKDGFDLNKGIEAKIHTLLPWQCTNGSEVQSSWAETT
YWISPQGIPETKVQDMDCVYYNWQYLLCSWKPGIGVLLDTN
YNLFYWYEGLDHALQCVDYIKADGQNIGCRFPYLEASDYKD
FYICVNGSSENKPIRSSYFTFQLQNIVKPLPPVYLTFTRESSCEI
KLKWSIPLGPIPARCFDYEIEIREDDTTLVTATVENETYTLKTT
NETRQLCFVVRSKVNIYCSDDGIWSEWSDKQCWEGEDLSKK
TLLRFWLPFGFILILVIFVTGLLLRKPNTYPKMIPEFFCDT

Fig. 1 ggtgcctgtc ggcggggaga gaggcaatat caaggtttta aatctcggag aaatggcttt cgtttgcttg gctatcggat
gcttatatac ctttctgata agcacaacat ttggctgtac ttcatcttca gacaccgaga taaaagttaa ccctcctcag
gatttgaga tagtggatcc cggatactta ggttatctct atttgcaatg gcaaccccca ctgtcctctgg atcatttaa
ggaatgcaca gtggaatatg aactaaaata ccgaacatt ggtagtgaaa catggaagac catcattact aagaatctac
attacaaaga tgggtttgat cttaacaagg gcattgaagc gaagatacac acgctttac catggcaatg cacaaatgga
tcagaagttc aaagttcctg ggcagaaact acttattgga tatcaccaca aggaattcca gaaactaaag ttcaggatat
ggattgcgta tattacaatt ggcaatattt actctgttct tggaaacctg gcataggtgt actctcttgat accaattaca acttgtttta
ctggtatgag ggcttggatc atgcattaca gtgtgttgaa ctgatgcaagg ctgatggaca aaatatagga tgcagatttc
cctatttgga ggcatcagac tataaagatt tctatatttg tgttaatgga tcatcagaga acaagcctat cagatccagt tatttcactt
ttcagcttca aaatatagtt aaacctttgc cgccagtcta tcttacttt actcgggaga gttcatgtga aattaagctg
aaatggagca tacctttggg acctattcca gcaaggtgtt ttgattatga aattgagatc agagaagatg atactacctt
ggtgactgct acagttgaaa atgaaacata caccttgaaa acaacaaatg aaacccgaca attatgcttt gtagtaagaa
gcaaagtgaa tattattgc tcagatgacg gaatttggagt gataaacaat gctgggaagg tgaagaccta
tcgaagaaaa ctttgctacg tttctggcta ccatttggtt tcatcttaat attagttata ttgtaaccg gtctgctttt gcgtaagcca
aacacctacc caaaaatgat tccagaattt ttctgtgata catgaagact ttccatatca agagacatgg tattgactca
acagtttcca gtcatggcca aatgtcaat atgagtctca ataaactgaa tttttcttgc gaatgttg

Fig. 2

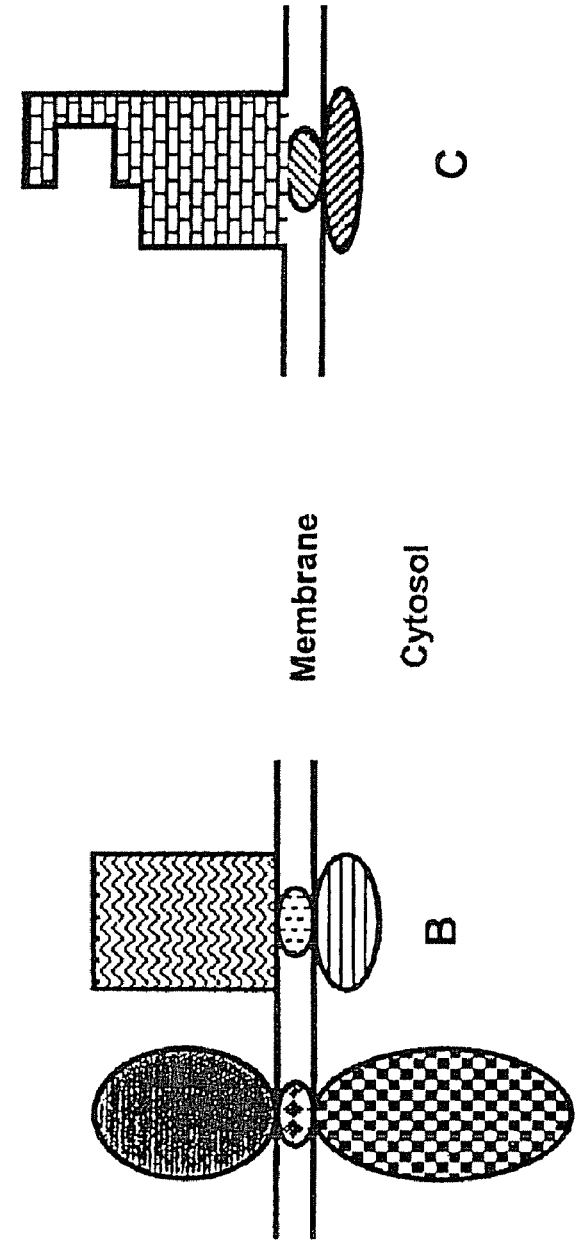

NUCLEIC ACID CANCER IMMUNOTHERAPY

CROSS REFERENCE TO RELATED APPLICATION

The present application is a divisional of U.S. patent application Ser. No. 10/104,408 filed Mar. 22, 2002 which is a continuation-in-part of U.S. patent application Ser. No. 09/780,926 filed Feb. 8, 2001 which claims the benefit of U.S. provisional application Ser. No. 60/181,000 filed Feb. 8, 2000.

STATEMENT AS TO FEDERALLY SPONSORED RESEARCH

This invention was made with Government support under grant number CA74145, awarded by the National Institutes of Health. The Government has certain rights in the invention.

FIELD OF THE INVENTION

The invention relates generally to the fields of biology, immunology, medicine, and oncology. More particularly, the invention relates to the use of the interleukin 13 (IL-13) receptor subunit alpha 2 (IL-13Rα2) as an immune system modulator and target for vaccines for the treatment and prevention of cancer.

BACKGROUND

Cancer is presently the second leading cause of death in developed nations. Wingo et al., J. Reg. Management, 25:43-51 (1998). Despite recent research that has revealed many of the molecular mechanisms of tumorigenesis, few new treatments have achieved widespread clinical success in treating solid tumors. The mainstay treatments for most malignancies thus remain gross resection, chemotherapy, and radiotherapy. While increasingly successful, each of these treatments still causes numerous undesired side effects. The primary cause of this is that none of these conventional methods specifically targets only diseased cells. For example, surgery results in pain, traumatic injury to healthy tissue, and scarring. Radiotherapy and chemotherapy cause nausea, immune suppression, gastric ulceration and secondary tumorigenesis.

In an effort to develop techniques to more specifically target diseased cells, progress in tumor immunology has led to the discovery of antigens that are preferentially or specifically expressed on cancer cells. These tumor-associated antigens (TAA) or tumor-specific antigens (TSA) have been used as antigenic agents in cancer vaccines designed to stimulate an immune response selectively directed against cancer cells expressing such antigens. See, *Tumor Immunology: Immunotherapy and Cancer Vaccines*, A. G. Dalgleish and M. J. Browning, eds., Cambridge University Press, 1996; *Immunotherapy in Cancer*, M. Gore and P. Riches, eds., John Wiley & Son Ltd., 1996; Maeurer et al., Melanoma Res., 6:11-24 (1996). Among the most widely studied of these antigens are melanoma associated antigens, prostate specific antigen (PSA), E6 and E7, carcinoembryonic antigen (CEA), p53, and gangliosides (e.g., GM2). More recent studies have shown that certain TAAs and TSAs are particularly effective at stimulating specific immune responses.

For example, pioneering research with melanoma associated antigens led to the identification of MAGE-1 (Melanoma Antigen 1) as a T-cell activating TSA. Traversari et al., Immunogenetics, 35: 145-152, 1992. Subsequently other groups using similar techniques identified other T-cell activating melanoma antigens including other MAGEs, MART-1, glycoprotein 100 (gp 100), tyrosinase, BAGE, and GAGE. Reviewed by Maeurer et al., supra. One of the most exciting recent findings in cancer immunology came after the SEREX (for serological analysis of recombinant cDNA expression libraries) technique was developed. Sahin et al., Proc. Natl. Acad. Sci. USA, 92: 11810-11813, 1995. The SEREX technique involves screening a cDNA expression library of an autologous tumor by exposing the library to antibodies contained in a patient's sera. Several active cancer antigens have been identified using this technique. See, Old, L. J. and T. C. Chen, J. Exp. Med., 187: 1163-1167, 1998. Moreover, SEREX analysis showed that patients produce a high titer of IgG antibodies against cancer antigens—a finding that indicated that helper T cells (e.g., CD4+ T cells) and B cells cooperate in stimulating an immune response against the cancer.

In addition, SEREX analyses led to the identification of a group of cancer antigens termed "cancer/testis" antigens (CTAs). CTAs share several common features including (a) among normal organs, almost exclusive expression in the testis, (b) expression in a wide variety of tumors, (c) presence of multiple members in each identified family, and (d) localization of their genes to the X chromosome (with the notable exception of SCP 1). Chen et al., J. Biol. Chem., 273: 17618-17625, 1998. Based on the foregoing criteria, several previously identified TAAs or TSAs (e.g., MAGE, BAGE and GAGE) were re-discovered as CTAs. Notably, unlike many non-CTA antigens, most of these previously identified CTAs as well as newly identified CTAs (e.g., SSX2, NY-ESO-1, SCP1 and CT7) have unequivocally been shown to stimulate an immune response in a subject.

SUMMARY

The invention relates to the discovery that IL-13Rα2 is a cancer/testis antigen. This discovery is important because, in contrast to most other cancer-associated agents, most of the cancer/testis antigens so far tested as active immunotherapy agents against cancer have proven very effective in stimulating anti-cancer immune responses in subjects. Thus, the present discovery provides methods and compositions for preventing and/or treating cancers that express IL-13Rα2.

In particular, the invention relates to the treatment and/or prevention of high-grade gliomas (HGG) in a subject as HGG cells have been shown to express high levels of IL-13Rα2 on their surfaces. Human HGG are rapidly progressing heterogeneous brain tumors of astroglial origin. The present invention is especially important because no effective modalities for treating HGG are yet accepted for clinical use. Previously, it was shown that the vast majority of HGG patients overexpress a more restrictive receptor for IL-13, that is a receptor that binds IL-13 in an IL-4 independent manner. Recently, a new IL-13 binding protein, termed IL-13Rα2, was cloned. This protein was shown to have affinity for IL-13 but not IL-4. In a rough comparison, this characteristic relates to the more restrictive receptor for IL-13 expressed on HGG. Here we demonstrate that, IL-13Rα2 serves as a selective target for HGG and other cancers that express IL-13Rα2 because, as described in more detail below, with the exception of testis, normal human tissue expresses little or no IL-13Rα2. And although many normal tissues express a receptor that binds IL-13, this receptor (sometimes termed the "shared" receptor because it binds both IL-13 and IL-4) differs functionally from IL-13Rα2 (believed to be the "restrictive" receptor) in that the shared receptor binds both IL-13 and IL-4, while the restrictive receptor binds only IL-13. The two receptors also differ structurally, with the restrictive receptor being a 42 kDa monomer and the shared receptor being a heterodimer composed of a 45 kDa component (termed IL-13Rα1) and a 140 kDa component (termed IL-4Rα).

As indicated above, our tissue distributions studies showed that, among normal tissues, IL-13Rα2 is strongly expressed only in testis. This finding along with the showing that (a) IL-13Rα2 is preferentially over-expressed on HGG but not normal central nervous system (CNS) tissue and (b) that the IL-13Rα2 gene is localized to chromosome X, indicates that IL-13Rα2 is a CTA. Because other CTAs, such as MAGE and BAGE, have proven to stimulate a strong immune response against cancer cells (see Mintz and Debinski in Crit. Rev. Oncogen 11:77-95; 2000), the present invention provides methods and compositions useful for generating or increasing an anti-cancer immune response in a subject.

For the purpose of anti-cancer immunotherapy, IL-13Rα2 has the following distinct advantages over other cancer-related antigens. Firstly, IL-13Rα2 is a cell-surface receptor, affording it exposure to the humoral arm of the immune system. Secondly, IL-13Rα2 is expressed on the vast majority of HGGs tested, indicating its critical role in HGG progression and its potential as a target for immunotherapy. Thirdly, the physiological distribution of IL-13Rα2 is limited to cancer cells and the testes, limiting the potential for autoimmune side affects that are observed when the target is also expressed in healthy tissue. Furthermore, autoimmune side affects are unlikely because the testes are an immune-privileged organ that expresses little MHC class I molecules. Fourthly, hIL-13Rα2 is an ideal target for anti-cancer immunotherapy because of its size (380 amino acids in full length IL-13Rα2 and 343 amino acids in the extracellular domain), providing the immune system with multiple epitopes to recognize and target.

Accordingly, in one aspect the invention features a method for stimulating a immune response against IL-13Rα2 in a subject having or at risk for developing a disease having cells expressing IL-13Rα2. The method includes the steps of: (a) formulating an anti-cancer vaccine outside of the subject, the vaccine including an agent that can stimulate an immune response against IL-13Rα2 when administered to an animal; and (b) administering the vaccine to the subject in an amount sufficient to stimulate an immune response against IL-13Rα2 in the subject.

In another aspect the invention features a composition for stimulating an immune response against IL-13Rα2 when administered to an animal. The composition includes: (a) an isolated agent that can stimulate an immune response against, IL-13Rα2 when administered to an animal; and (b) a pharmaceutically acceptable carrier.

In both of the foregoing method and composition, the agent that can stimulate an immune response against IL-13Rα2 can include a peptide including at least seven contiguous amino acids of SEQ ID NO:1. For example, the agent can be a protein including the amino acid sequence of SEQ ID NO:1. The agent can also take the form of a nucleic acid that nucleic acid can be used as a naked DNA or in an expression vector construct including the nucleic acid. The agent that can stimulate an immune response against IL-13Rα2 can also be a cell. This cell can be one that expresses a peptide including at least seven contiguous amino acids of SEQ ID NO:1, or one into which a purified nucleic acid that encodes a peptide including at least seven contiguous amino acids of SEQ ID NO:1 has been introduced.

The vaccines and compositions within the invention can further include an adjuvant such as an aluminum salt; an oil-in-water emulsion; a composition including saponin; a composition including a bacterial protein; or a cytokine.

The method of the invention can further include a step of providing a subject (e.g., a human being) having or at risk for developing a cancer having cells expressing IL-13Rα2 (e.g., glioma cells). Also in the method, the step of administering the vaccine to the subject in an amount sufficient to stimulate an immune response against IL-13Rα2 in the subject can include administering the vaccine in at least a first dose and a second dose, wherein the first dose is administered to the subject at least 24 hours before the second dose is administered to the subject.

Unless otherwise defined, all technical terms used herein have the same meaning as commonly understood by one of ordinary skill in the art to which this invention belongs. Definitions of molecular biology terms can be found, for example, in Rieger et al., Glossary of Genetics: Classical and Molecular, 5th edition, Springer-Verlag: New York, 1991; and Lewin, Genes V, Oxford University Press: New York, 1994. Standard one-letter nomenclature for nucleotide bases, and one- and three-letter nomenclature for amino acid residues are used.

As used herein, a "nucleic acid" means a chain of two or more nucleotides. For example, RNA (ribonucleic acid) and DNA (deoxyribonucleic acid) are nucleic acids. An "isolated" nucleic acid is one that has been substantially separated or purified away from other nucleic acid sequences in the cell of the organism in which the nucleic acid naturally occurs, i.e., other chromosomal and extrachromosomal DNA and RNA, e.g., by conventional nucleic acid purification methods. The term therefore includes a recombinant nucleic acid molecule incorporated into a vector, into an autonomously replicating plasmid or virus, or into the genomic DNA of a prokaryote or eukaryote. It includes a separate molecule such as a cDNA, a genomic fragment, a fragment produced by polymerase chain reaction (PCR), or a restriction fragment. It also includes recombinant nucleic acid molecules and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

When referring to a nucleic acid molecule or polypeptide, the term "native" refers to a naturally-occurring (e.g., a "wild-type") nucleic acid or polypeptide. A "homolog" of an IL-13Rα2 gene is a gene sequence encoding an IL-13Rα2 polypeptide isolated from a species other than Homo sapiens. By the phrase "naked nucleic acid" is meant an isolated nucleic acid not incorporated in an expression vector.

By the terms "IL-13Rα2 gene" or "IL-13Rα2 polynucleotide" is meant a native IL-13Rα2 encoding nucleic acid sequence (e.g., the IL-13Rα2 cDNA sequence shown as SEQ ID NO: 2 (FIG. 2)), genomic sequences from which IL-13Rα2 cDNA can be transcribed, and/or allelic variants and homologs of the foregoing.

As used herein, "protein," "peptide," or "polypeptide" means any peptide-linked chain of amino acids, regardless of length or post-translational modification, e.g., glycosylation or phosphorylation. Generally, the term "peptide" is used herein to refer to amino acid chains less than about 25 amino acid residues in length, while the terms "protein" and "polypeptide" are used to refer to larger amino acid chains. When referring to a protein or peptide, the term "isolated" means proteins or peptides that are isolated from other cellular proteins or are made synthetically. The term thus encompasses both purified and recombinant polypeptides. The term "recombinant protein" or "recombinant peptide" refers to a protein or peptide that is produced by recombinant nucleic acid techniques, wherein generally, a nucleic acid encoding the peptide or protein is inserted into a suitable expression vector which is in turn used to transform a host cell such that, when cultured under appropriate conditions, the cell produces the peptide or protein.

By "IL-13Rα2 protein" "IL-13Rα2 polypeptide," or simply "IL-13Rα2" is meant an expression product of an IL-13Rα2 gene such as the protein of SEQ ID NO:1 (FIG. 1); or a protein that shares at least 65% (but preferably 75, 80, 85, 90, 95, 96, 97, 98, or 99%) amino acid sequence identity with SEQ ID NO:1 and cross-reacts with antibodies that specifically bind the protein of SEQ ID NO:1.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

As used herein, the term "vector" refers to a nucleic acid molecule capable of transporting another nucleic acid to which it has been linked. A vector capable of directing the expression of a gene to which it is operatively linked is referred to herein as an "expression vector." As used herein, the term "promoter" means a nucleic acid sequence that regulates expression of a selected nucleic acid sequence operably linked to the promoter, and which effects expression of the selected nucleic acid sequence in cells. The term encompasses "tissue specific" promoters, i.e. promoters, which effect expression of the selected nucleic acid sequence only in specific cells (e.g. cells of a specific tissue). The term also covers so-called "leaky" promoters, which regulate expression of a selected nucleic acid primarily in one tissue, but cause expression in other tissues as well. The term also encompasses both non-tissue specific promoters and promoters that are constitutively active and inducible.

By the phrase "stimulating an immune response" is meant eliciting or increasing the activation of a lymphocyte (e.g., a B cell or T cell) or other immune system component. The stimulation of an immune response against a specific antigen can be measured as an increase in antibody titer against that antigen or the activation of one or more lymphocytes having a surface receptor specific for the antigen. Activation of lymphocytes can be determined by conventional assays, e.g., the induction of mitosis, secretion of cytokines, modulation of cell surface molecule expression, secretion of immunoglobulin (B cells), and increased killing of target cells (cytotoxic T cells).

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ liters/mole for that second molecule.

By the term "antibody" is meant any antigen-binding peptide derived from an immunoglobulin. The term includes polyclonal antisera, monoclonal antibodies, fragments of immunoglobulins produced by enzymatic digestion (e.g., Fab fragments) or genetic engineering (e.g., sFv fragments).

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1 is the amino acid sequence of the native *H. sapiens* IL-13Rα2 protein.

FIG. 2 is the nucleic acid sequence of a cDNA corresponding to a native mRNA encoding the native *H. sapiens* IL-13Rα2 protein.

FIG. 3 is a schematic representation of two types of IL-13 receptors: the shared with IL-4 physiological, heterodimeric IL-13/4R, and an IL-4-independent monomeric, HGG-associated IL-13R. A, 140-kDa IL-4R α-chain. B, 45-kDa IL-13R α1-chain; A and B constitute the elements of the heterodimeric high affinity IL-13/4R. C, a 42-kDa monomer of IL-13Rα2.

DETAILED DESCRIPTION

Figure 4:
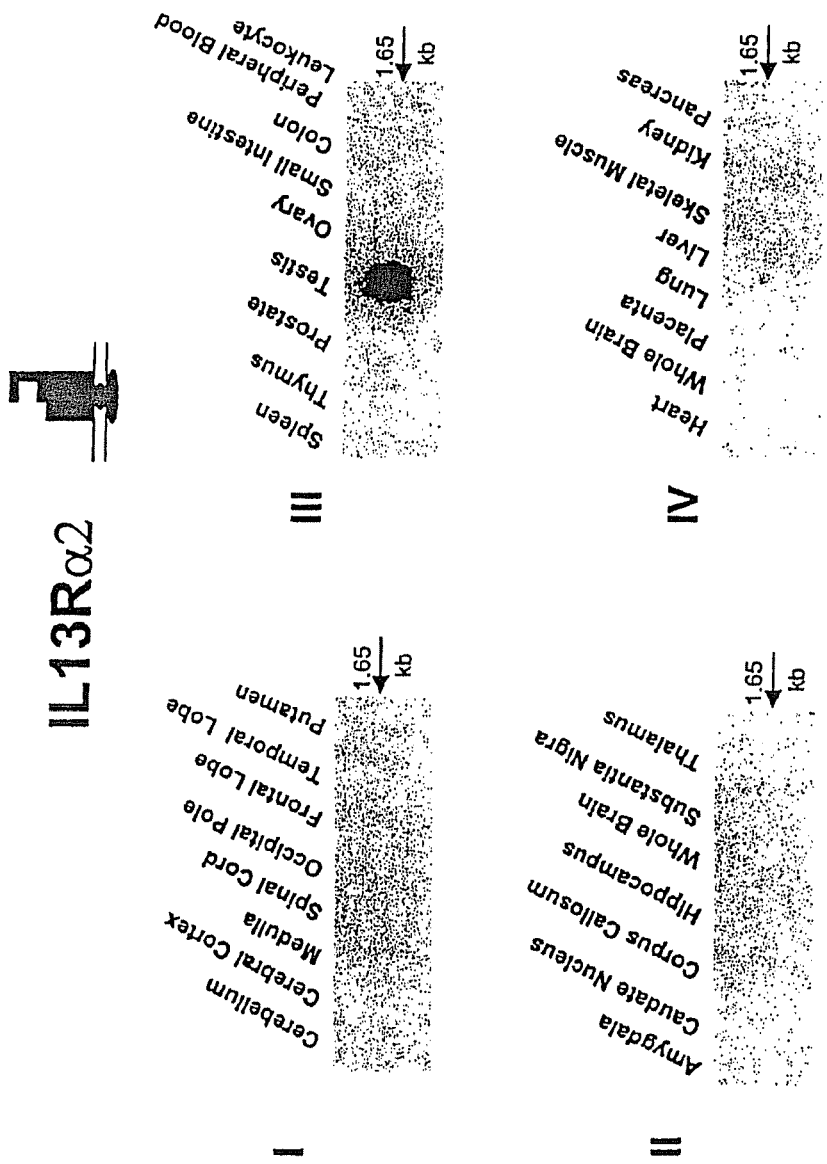
FIG. 4 is a Northern blot analysis of human IL-13Rα2 transcripts (closed figure) in series of CNS (panels I and II) and peripheral tissues (panels III and IV). The migration position of mRNA is shown in kilobases. Films were exposed for 2 weeks.

The invention encompasses compositions and methods relating to stimulating an immune response against IL-13Rα2 in a subject having or being at risk for developing a cancer or other disease having cells expressing IL-13Rα2. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Identification of IL-13Rα2 as a Cancer/Testis Antigen As its name implies, IL-13Rα2 is a receptor for the lymphokine IL-13. IL-13 has been identified as a homologue of IL-4 that is secreted by both B and T cells. Minty et al., Nature, 36: 248-251, 1993; McKenzie et al., Proc. Natl. Acad. Sci. USA, 90: 3735-3739, 1993. Several types of normal cells contain an IL-13 receptor termed the shared IL-13/IL-4 receptor, which is a heterodimer that includes an IL-13 binding subcomponent named IL-13Rα1 (Interleukin 13 receptor alpha one). Hilton et al., Proc. Natl. Acad. Sci. USA, 93: 497-501, 1996; Aman et al., J. Biol. Chem., 271: 29265-29270, 1996; Miloux et al., FEBS Letters, 40: 163-166, 1997. In addition to IL-13Rα1, the shared receptor also includes a protein referred to as p140 (or IL-4Rα), the subcomponent responsible for IL-4 binding. Idzerda et al., J. Exp. Med., 171: 861-873, 1990; Hilton et al., Proc. Natl. Acad. Sci. USA, 93: 497-501, 1996; Debinski et al., Nature Biotech., 16: 449-453, 1995; Zurawski et al., EMBO J., 12: 2663-2670, 1993; Minty et al., Nature, 36: 248-251, 1993. Exposing cells to IL-13 results in responses very similar to those responses that occur after exposure to IL-4. Zurawski, G., and J. E. de Vries, Stem Cells. 12: 169-174, 1994. Examples of cellular responses resulting from both IL-13 and IL-4 exposure include enhanced expression of CD72, IgM, and MHC class II antigen, as well as induced CD23 expression and IgE heavy-chain gene production in B lymphocytes. Id.

In an interesting development, it was found that IL-13Rα1 was not the only IL-13 binding site that existed on cells. In previous studies, it was demonstrated that many cancers, most notably HGG, are capable of binding IL-13. Debinski et al., Clin. Cancer Res., 1:1253-1258, 1995; Debinski et al., J. Biol. Chem., 271: 22428-22433, 1996; Debinski et al., Nature Biotech., 16: 449-453, 1998; Debinski et al., Critic Rev. Oncogen., 9: 256-268, 1998; Debinski et al., Clin. Cancer Res., 5: 985-990, 1999. Through these studies, it became increasingly clear that the IL-13 binding capacity of many of these tumors was not mediated through the shared IL-13/IL-4 receptor (i.e., the receptor now known to be a heterodimer composed of IL-13Rα1/p140). Notably, in lymphoid cells that contain the shared-receptor, saturating the receptors with IL-4 blocked IL-13 binding. Zurawski et al., EMBO J., 12: 2663-2670, 1993. This was not the case using HGG cells, where IL-13 binding was unaltered even where a large excess of IL-4 used in neutralization assays. Debinski et al., Clin. Research Res., 1: 1253-1258, 1995; Debinski et al., J. Biol. Chem., 271: 22428-22433, 1996; Debinski et al., Nature Biotech., 16: 449-453, 1998. In further experiments, rationally designed IL-13 mutants were generated that maintained their ability to bind glioblastoma (HGG) cells but lost their ability to interact and cause signaling in cells expressing only the IL-4/IL-13 shared receptor. Debinski et al., Nature Biotech., 16: 449-453, 1998; Thompson, J. P. and W. Debinski, J. Biol. Chem., 274: 29944-29950, 1999; Debinski, W., and J. P. Thompson, Clin. Cancer Res., 5: 3143s-3147s, 1999. This evidence supported the existence of an additional IL-13 binding protein, unrelated to known IL-4 binding proteins. Additional evidence was derived when a novel IL-13 binding protein on cells of renal cell carcinoma metastases (Caki-1 cells) was isolated and the gene encoding the protein cloned. Caput et al., J. Biol. Chem., 271:16921, 1996. The gene encoding this protein, termed IL-13Rα2, was subsequently cloned and sequenced. Id. This novel IL-13 binding protein, referred to herein as IL-13Rα2, was shown not to specifically bind IL-4. The proposed structures of the shared IL-13/4 receptor and the IL-4-independent receptor for IL-13 are shown in FIG. 3.

To investigate whether this newly discovered receptor is present in HGG, we evaluated its gene expression in HGG established cell lines, and HGG explant cells and tumor specimens. In addition to these studies on HGG, we screened a plethora of normal central nervous system (CNS) tissues and peripheral organs for the mRNA transcripts of IL-13Rα2 in order to characterize the normal tissue expression pattern of this new receptor in detail. From these studies, we discovered that IL-13Rα2 expression is virtually absent in all normal adult tissue except testis. In earlier studies, the gene encoding IL-13Rα2 was localized to the X chromosome. Guo et al., Genomics, 42: 141-145, 1997.

Accordingly, our discovery allowed us to characterize the IL-13Rα2 protein as a member of the CTA group of tumor antigens. Moreover, because IL-13Rα2 is a transmembrane receptor, it is exposed to the extracellular environment independently of MHC presentation. Thus, in contrast to intracellular antigens that must be displayed as a peptide fragment in complex with an MHC molecule on the cell surface to be recognized by immune system components, cytotoxic agents or antibodies can be directly targeted to cancer cells bearing IL-13Rα2 on their surface. This discovery that IL-13Rα2 is a CTA associated with HGG is significant because no other HGG-associated antigens of this prevalence are known that could serve as a basis for a rational design of anti-glioma vaccines.

Vaccines

The invention provides vaccines that can stimulate an immune response against IL-13Rα2 in a subject when administered to the subject. Vaccines within the invention include an antigenic agent which can take the form of any substance that can evoke or increase an immune response against IL-13Rα2 when introduced into a subject. Typical immune responses include (a) the production of, or increase in titer of, antibodies that specifically bind IL-13Rα2 and (b) the activation of T lymphocytes (e.g., to kill a target cell or provide help in the activation of antibody production in B lymphocytes). A number of different antigenic agents have been shown to be effective in stimulating an immune response against a protein antigen, including, for example, protein- and peptide-based vaccines, tumor-cell vaccines, dendritic cell/gene therapy vaccines and DNA/viral vaccines. See, e.g., Greten, T. F. and E. M. Jaffee, J. Clin. Oncol., 17: 1047-1060, 1999. In addition to the foregoing, various substances such as adjuvants and excipients/carriers can be included in the vaccine compositions of the invention to non-specifically enhance the antigen-specific immune response stimulated by the antigenic agent and to facilitate delivery of the other components of the vaccine to a subject.

Protein/Peptide Based Vaccines

The antigenic agent for use in the vaccines of the invention can take the form of the native IL-13Rα2 (SEQ ID NO:1) or a peptide fragment of IL-13Rα2. Vaccines made with the whole protein antigen are advantageous because they have the capability of stimulating an immune response against all of the potential antigenic sites expressed by the protein. Vaccines made with peptide antigens (e.g., 7-15 or 8-12 contiguous amino acids of the whole protein), on the other hand, will generally stimulate an immune response against fewer than all of the potential antigenic sites expressed by the protein. Peptide-based vaccines are sometimes advantageous over whole protein-based vaccines where it is desired to more specifically target the stimulated immune response, e.g., to avoid undesired cross reactions. For example, peptides for use in the vaccine can be selected to correspond to (1) specific epitopes of the antigens that are known to be presented by MHC class I or MHC class II molecules, or (2) a modified form of an epitope that either exhibits an increased stability in vivo or a higher binding affinity for an MHC molecule than the native epitope, while still being capable of specific activation of T-cells. See, Ayyoub et al., J. Biol. Chem., 274: 10227-10234, 1999; Parkhurst et al., Immunol., 157: 2539-2548, 1996. Peptide-based vaccines have been shown to circumvent immune tolerance to the intact proteins. Disis et al., J. Immunol., 156: 3151-3158, 1996. In addition to vaccines composed of only one type of peptide fragment, other vaccines within the invention also include those made up of a cocktail of several different peptides derived from IL-13Rα2.

As indicated above, vaccines with in the invention can include an IL-13Rα2 protein as an antigenic agent. Preferred forms of IL-13Rα2 protein include a purified native IL-13Rα2 protein that has the amino acid sequence shown in FIG. 1 (SEQ ID NO:1). Variants of the native IL-13Rα2 protein such as fragments, analogs and derivatives of native IL-13Rα2 are also contemplated for use as an antigenic agent in the vaccines of the invention. Such variants include, e.g., a polypeptide encoded by a naturally occurring allelic variant of the native IL-13Rα2 gene, a polypeptide encoded by a homolog of the native IL-13Rα2 gene, and a polypeptide encoded by a non-naturally occurring variant of the native IL-13Rα2 gene. Preferred versions of such variants are those that are able to stimulate an immune response to native IL-13Rα2 upon administration to a subject as part of a vaccine.

IL-13Rα2 protein variants have a peptide sequence that differs from the native IL-13Rα2 protein in one or more amino acids. The peptide sequence of such variants can feature a deletion, addition, or substitution of one or more amino acids of the native IL-13Rα2 polypeptide. Amino acid insertions are preferably of about 1 to 4 contiguous amino acids, and deletions are preferably of about 1 to 10 contiguous amino acids. In some applications, variant IL-13Rα2 proteins substantially maintain a native IL-13Rα2 protein functional activity (e.g., the ability to specifically bind IL-13). For other applications, variant IL-13Rα2 proteins lack or feature a significant reduction in an IL-13Rα2 protein functional activity. Where it is desired to retain a functional activity of native IL-13Rα2 protein, preferred IL-13Rα2 protein variants can be made by expressing nucleic acid molecules within the invention that feature silent or conservative changes. Variant IL-13Rα2 proteins with substantial changes in functional activity can be made by expressing nucleic acid molecules within the invention that feature less than conservative changes.

IL-13Rα2 protein fragments corresponding to one or more particular motifs (e.g., those likely to bind with high affinity to MHC molecules) and/or domains are within the invention as are those of arbitrary sizes. For example, peptide fragments of IL-13Rα2 protein consisting of at least 5, 10, 25, 30, 40, 50, 50, 70, 75, 80, 90, 100, 110, 120, 130, 140, 150, 160, 170, 180, 190, 200, 210, 220, 230, 240, 250, 260, 270, 280, 300 or more contiguous amino acids of the IL-13Rα2 protein are within the scope of the present invention. Fragments of between 7 and 15 amino acids (preferably 8-12 amino acids) in length (e.g., those sized to fit in the grooves of MHC molecules) are preferred as peptides of such size have been shown to serve as efficient immunogenic agents. Methods for identifying efficiently immunogenic peptides of a whole protein are known in the art, e.g., using amphipathicity algorithms. See, e.g., Berzofsky, J. A., Ann. N.Y. Acad. Sci., 12:256, 1993; U.S. Pat. Nos. 5,976,541 and 5,980,899. Peptides that are most immunogenic in a subject can also be determined by preparing a series of overlapping peptide fragments (e.g., 7-30 amino contiguous amino acids long) of the whole antigen, administering the subject (or a series of genetically similar such subjects) such fragments in a vaccine composition, and analyzing the subject(s) for the stimulation of an immune response. Those peptide fragments that induce the desired response can then be selected.

Isolated peptidyl portions of IL-13Rα2 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, similar to the technique described above, an IL-13Rα2 protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function antigenic agents that stimulate an immune response against an IL-13Rα2 protein.

Another aspect of the present invention concerns recombinant forms of the IL-13Rα2 proteins. Recombinant polypeptides preferred for use in the present invention, in addition to native IL-13Rα2 protein, are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of SEQ ID NO:2. In a preferred embodiment, variant IL-13Rα2 have the ability to stimulate an immune response against the native IL-13Rα2 protein. IL-13Rα2 protein variants can be generated through various techniques known in the art. For example, IL-13Rα2 protein variants can be made by mutagenesis, such as by introducing discrete point mutation(s), or by truncation. Mutation can give rise to an IL-13Rα2 protein variant having more, substantially the same, or merely a subset of the antigenic activity of the native IL-13Rα2 protein. Other variants of IL-13Rα2 that can be generated include those that are resistant or more susceptible to proteolytic cleavage, as for example, due to mutations which alter protease target sequences. Whether a change in the amino acid sequence of a peptide results in a IL-13Rα2 protein variant having greater or lesser antigenic activity than native IL-13Rα2 protein can be readily determined by comparing the variant with the native IL-13Rα2 protein for the ability to stimulate an immune response against IL-13Rα2 in subjects vaccinated with the respective proteins.

As another example, IL-13Rα2 protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential IL-13Rα2 protein sequences. The synthesis of degenerate oligonucleotides is well known in the art (see for example, Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) Proc. Natl. Acad. Sci. USA 89:2429-2433; Devlin et al. (1990) Science 249: 404-406; Cwirla et al. (1990) Proc. Natl. Acad. Sci. USA 87: 6378-6382; as well as U.S. Pat. Nos. 5,223,409; 5,198,346; and 5,096,815). Similarly, a library of coding sequence fragments can be provided for an IL-13Rα2 gene clone in order to generate a variegated population of IL-13Rα2 protein fragments for screening and subsequent selection of fragments having the ability to stimulate an immune response against IL-13Rα2 in a subject. A variety of techniques are known in the art for generating such libraries, including chemical synthesis. In one embodiment, a library of coding sequence fragments can be generated by (i) treating a double-stranded PCR fragment of an IL-13Rα2 gene coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes. The invention also provides for reduction of IL-13Rα2 proteins to generate mimetics, e.g. peptide or non-peptide agents, that are able to stimulate an immune response against IL-13Rα2 in a subject. For instance, non-hydrolyzable peptide analogs of the amino acid residues of IL-13Rα2 proteins and peptides thereof can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1:1231), and b-aminoalcohols (Gordon et al. (1985) Biochem. Biophys. Res. Commun. 126:419; and Dann et al. (1986) Biochem. Biophys. Res. Commun. 134:71). IL-13Rα2 proteins may also be chemically modified to create IL-13Rα2 derivatives by forming covalent or aggregate conjugates with other chemical moieties, such as glycosyl groups, lipids, phosphate, acetyl groups and the like. Covalent derivatives of IL-13Rα2 proteins or peptides can be prepared by linking the chemical moieties to functional groups on amino acid side chains of the protein/peptide or at the N-terminus or at the C-terminus of the protein/peptide.

IL-13Rα2 proteins may also be fused to one or more other proteins. For example, an IL-13Rα2 protein or immunogenic portion thereof may be fused to another protein that serves as a targeting ligand to deliver the IL-13Rα2 protein or portion to a particular target site in a subject (e.g., in order to stimulate a local immune response at that site). For instance, an IL-13Rα2 protein or peptide can be fused to a mutant IL-13 molecule or anti-IL-13 receptor antibody to specifically target the IL-13Rα2 protein or peptide to a tumor, e.g., a HGG. As another example, to enhance immunogenicity of the antigen, an IL-13Rα2 protein or peptide is fused to a toxoid such as one derived from a *Pseudomonas* (e.g., D553) or Diphtheria exotoxin.

Numerous methods of fusing two or more proteins together are known in the art, e.g., making and expressing a recombinant fusion construct, or using a cross-linking agent to covalently bond the two or more proteins together to form one molecule. Any suitable for this application might be used in the invention. The IL-13Rα2 proteins and peptides of the invention can be made by known methods. For example, a host cell transfected with a nucleic acid vector directing expression of a nucleotide sequence encoding the subject proteins or peptides can be cultured under appropriate conditions to allow expression of the peptide to occur. The cells may be harvested, lysed, and the protein isolated. A recombinant IL-13Rα2 protein or peptide can be isolated from host cells using techniques known in the art for purifying proteins including ion-exchange chromatography, gel filtration chromatography, ultrafiltration, electrophoresis, and immunoaffinity purification with antibodies specific for such protein or peptide.

For example, after an IL-13Rα2 protein or peptide has been expressed in a cell, it can be isolated using immuno-affinity chromatography. For instance, an anti-IL-13Rα2 antibody that specifically binds the subject proteins or peptides can be immobilized on a column chromatography matrix, and the matrix can be used for immuno-affinity chromatography to purify the proteins or peptides from cell lysates by standard methods (see, e.g., Ausubel et al., supra).

After immuno-affinity chromatography, the proteins or peptides can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, the IL-13Rα2 proteins or peptides utilized in the invention are expressed as a fusion protein containing an affinity tag (e.g., GST) that facilitates its purification.

In association with an antigenic agent (e.g., a IL-13Rα2 protein or peptide fragment thereof) of a vaccine of the invention, an adjuvant can be used to boost the immune response. Suitable adjuvants for use in the invention can include any substance that can non-specifically enhance an antigen-specific immune response stimulated by an antigenic agent. Many such adjuvants are known, including for example: (1) Freund's adjuvant (complete and incomplete) (2) oil-in-water emulsion formulations such as the Ribi™ adjuvant system (Corixa, Seattle, Wash.) (3) aluminum salts (e.g., aluminum hydroxide, aluminum phosphate, aluminum sulfate, etc); (4) saponin-based adjuvants (Stimulon™ from Aquila Biosciences, Framingham, Mass.); (5) cytokines such as IL-1, IL-2, macrophage colony stimulating factor, and tumor necrosis factor; and (6) other substances that act as immuno-stimulating agents such as muramyl peptides or bacterial cell wall components, toxins, and toxoids.

To facilitate their formulation for administration to a subject, the vaccine compositions of the invention (e.g., the protein/peptide antigen and adjuvant) can further contain a pharmaceutically acceptable carrier or excipient. For example the protein/peptide antigen and adjuvant can be mixed with a diluent such as water, saline, glycerol, ethanol, etc. Other substances, such as preservatives, surfactants, emulsifying agents, buffers, etc. can also be included. Typically, the protein/peptide-based vaccine compositions of the invention are prepared for parenteral injection as liquid solutions or suspensions. The vaccine compositions can also be prepared as solids (e.g., a lyophilized powder) that can be reconstituted in a liquid (e.g., saline) prior to injection into a subject. The vaccine compositions can also be emulsified or encapsulated in liposomes.

Nucleic Acid-based Vaccines

Nucleic acid-based vaccines are known to elicit a prominent cell-mediated immune response. See, e.g., Donnely et al., 1997; Rosenberg, S. A., Immunity 10:281, 1999. Thus, in addition to protein/peptide based vaccines, the antigenic agent for use in the vaccines of the invention can take the form of a nucleic acid that can stimulate an immune response against IL-13Rα2 when administered to a subject. Examples of such nucleic acids include those that encode the native IL-13Rα2 such as the nucleic acid shown herein as SEQ ID NO:2 (FIG. 2), a variant of the native IL-13Rα2, or a peptide fragment of that native or variant IL-13Rα2. Vaccines made with a nucleic acid that encodes the whole protein antigen are advantageous because they have the potential for stimulating an immune response against all of the different antigenic sites expressed by the protein. Vaccines made with a nucleic acid that encodes a peptide antigen (e.g., 7-15 amino acids of the whole protein), on the other hand, will generally stimulate an immune response against fewer than all of the potential antigenic sites expressed by the protein.

The form of the nucleic acid used in a vaccine of the invention can be any suitable for stimulating an immune response against IL-13Rα2 when administered to a subject. For example, the nucleic acid can be in the form of "naked DNA" or it can be incorporated in an expression vector. A description of suitable nucleic acids is presented below.

Nucleic acids that are most immunogenic in a subject can be determined by preparing several of the below listed nucleic acids (e.g., those that encode the whole antigen or peptide fragments thereof), administering the subject (or a series of genetically similar such subjects) such nucleic acids in a vaccine composition (e.g., as naked nucleic acid or in an expression vector in a suitable carrier), and analyzing the subject(s) for the stimulation of an immune response. Those nucleic acids that induce the desired response can then be selected.

Nucleic acid molecules utilized in the present invention as an antigenic agent may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes the native IL-13Rα2 protein may be identical to the nucleotide sequence shown in FIG. 2. It may also be a different coding sequence which, as a result of the redundancy or degeneracy of the genetic code, encodes the same polypeptide as shown in SEQ ID NO:1 (FIG. 1).

Other nucleic acid molecules useful in the invention are variants of the native IL-13Rα2 gene such as those that encode fragments (e.g., post-translationally processed forms of), analogs and derivatives of a native IL-13Rα2 protein. Such variants may be, e.g., a naturally occurring allelic variant of the native IL-13Rα2 gene, a homolog of the native IL-13Rα2 gene, or a non-naturally occurring variant of the native IL-13Rα2 gene. These variants have a nucleotide sequence that differs from the native IL-13Rα2 gene in one or more bases. For example, the nucleotide sequence of such variants can feature a deletion, addition, or substitution of one or more nucleotides of the native IL-13Rα2 gene. Nucleic acid insertions are preferably of about 1 to 10 contiguous nucleotides, and deletions are preferably of about 1 to 30 contiguous nucleotides.

Naturally occurring allelic variants of the native IL-13Rα2 gene within the invention are nucleic acids isolated from human tissue that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native IL-13Rα2 gene, and encode polypeptides having structural similarity to native IL-13Rα2 protein. Homologs of the native IL-13Rα2 gene within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native IL-13Rα2 gene, and encode polypeptides having structural similarity to native IL-13Rα2 protein. Public and/or proprietary nucleic acid databases can be searched in an attempt to identify other nucleic acid molecules having a high percent (e.g., 70, 80, 90% or more) sequence identity to the native IL-13Rα2 gene.

Non-naturally occurring IL-13Rα2 gene variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native IL-13Rα2 gene, and encode polypeptides having structural similarity to native IL-13Rα2 protein. Examples of non-naturally occurring IL-13Rα2 gene variants are those that encode a fragment of a IL-13Rα2 protein, those that hybridize to the native IL-13Rα2 gene or a complement of to the native IL-13Rα2 gene under stringent conditions, those that share at least 65% sequence identity with the native IL-13Rα2 gene or a complement of the native IL-13Rα2 gene, and those that encode a IL-13Rα2 fusion protein.

Nucleic acids encoding fragments of native IL-13Rα2 protein within the invention are those that encode, e.g., 2, 5, 6, 7, 8, 9, 10, 11, 12, 13, 14, 15, 16, 17, 18, 19, 20, 25, 30, 40, 50, 60, 70, 80, 90, 100, 150, 200, 250, 300 or more amino acid residues of the native IL-13Rα2 protein. Shorter oligonucleotides (e.g., those of 6, 7, 8, 9, 10, 11, 12, 13, 14, 15, 16, 17, 18, 19, 20, 30, 50, 100, 125, 150, or 200 base pairs in length) that encode fragments of the native IL-13Rα2 protein can be used. Nucleic acids encoding fragments of native IL-13Rα2 protein can be made by enzymatic digestion (e.g., using a restriction enzyme) or chemical degradation of the full length native IL-13Rα2 gene or variants thereof.

Nucleic acid molecules encoding IL-13Rα2 fusion proteins are also within the invention. Such nucleic acids can be made by preparing a construct (e.g., an expression vector) that expresses a IL-13Rα2 fusion protein when introduced into a suitable host. For example, such a construct can be made by ligating a first polynucleotide encoding an IL-13Rα2 protein fused in frame with a second polynucleotide encoding another protein (e.g., a detectable label or carrier protein) such that expression of the construct in a suitable expression system yields a fusion protein. IL-13Rα2 fusion proteins can be used, e.g., to enhance the immunogenicity of IL-13Rα2 peptides, to facilitate purification of IL-13Rα2 proteins/peptides, or to track the location of the IL-13Rα2 fusion protein after it has been administered to a subject.

Using the nucleotide sequence of the native IL-13Rα2 gene and the amino acid sequence of a native IL-13Rα2 protein, those skilled in the art can create nucleic acid molecules that have minor variations in their nucleotide sequences, by, for example, standard nucleic acid mutagenesis techniques or by chemical synthesis. Variant IL-13Rα2 nucleic acid molecules can be expressed to produce variant IL-13Rα2 proteins.

Naked Nucleic Acid Vaccines

The invention provides for the use of naked nucleic acid vaccines to stimulate an immune response against IL-13Rα2. Representative naked nucleic acid vaccines for use in this method include a DNA encoding one or more immunogenic portions of IL-13Rα2 along with sufficient other 5' and 3' elements to direct expression of the foregoing. The use of naked nucleic acids for stimulating both class I and class II restricted immune responses against a particular protein is known in the art. See, e.g., Rosenberg, S. A., Immunity 10:281, 1999; Ulmer et al., Science, 259:1745, 1993; Donnelly et al., Ann. NY Acad. Sci., 772:40, 1995; Scheurs et al., Cancer res. 58:2509, 1998; Hurpin et al., Vaccine 16:208, 1998; Lekutis et al., J. Immunol. 158:4471, 1997; Manickan et al., J. Leukoc. Biol. 61:125, 1997. These methods can be adapted for use in the present invention by using a nucleic acid encoding one or more immunogenic portions of IL-13Rα2. Naked nucleic acid vaccines can be administered to a subject by any suitable technique. For example, naked DNA encoding a peptide portion of IL-13Rα2 can be injected into muscle cells of a subject or naked DNA-coated gold particles can be introduced into skin cells (to be taken up by dendritic cells) of a subject using a gene gun.

Expression Vector Vaccines

The invention also provides for the use of expression vector vaccines to stimulate an immune response against IL-13Rα2. In a typical application of this technique, a nucleic acid encoding one or more peptide or protein antigens of IL-13Rα2 is incorporated into a vector that allows expression of the antigen(s) in a host cell (e.g., a cell inside a subject or administered to a subject). The nucleic acid encoding the antigen(s) is generally be under the operational control of other sequences contained within the vector such as a promoter sequences (e.g., tissue specific, constitutively active, or inducible) or enhancer sequences. The antigen(s) encoded by the vector are expressed when the vector is introduced into a host cell in a subject. After expression, the antigen(s) can associate with an MHC molecule for presentation to immune system cells such as T lymphocytes, thus stimulating an immune response. See, e.g., Corr et al., J. Exp. Med. 184: 1555 (1996).

Vectors for use in the invention can be any capable of expressing an encoded antigen(s) in a subject. For example, vectors derived from bacterial plasmids and viruses may be used. Representative viral vectors include retroviral, adenoviral, and adeno-associated viral vectors. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Cell-Based Vaccines

Cell-based vaccines are provided in the invention to stimulate an immune response against IL-13Rα2. In similar approaches using different cancer-associated antigen, cancer cells isolated from a patient have been harbored in vitro and transfected with DNA encoding for immune stimulants, such as cytokines, MHC molecules or co-stimulatory molecules. The transfected cancer cells were then re-injected to the patient in order to activate the immune system in order to generate an anti-cancer response. Greten, T. F., and E. M. Jaffee, J. Clin. Oncol., 17: 1047-1060, 1999; Simons et al., Cancer Res., 57: 1537-1546, 1997.

The invention further provides an isolated cell expressing IL-13Rα2 or a peptide fragment of IL-13Rα2. Cells expressing IL-13Rα2 can be isolated from a subject having such cells (e.g., from testis or HGG). Cells that do not express IL-13Rα2 can be made to express this protein in a number of different ways. As one example, cells can be cultured with IL-13Rα2 or peptide fragments thereof under conditions in which fragments of IL-13Rα2 become associated with MHC molecules on the cell surface. Alternatively, cells can be made to express IL-13Rα2 by introducing a nucleic acid encoding an IL-13Rα2 protein, a peptide fragment of IL-13Rα2, or a variant of the foregoing into the cells, and culturing such cells under conditions that cause the cells to express the protein or peptide. Cellular expression of the protein, peptide, or variant can be monitored by any conventional technique. For example, fluorescently labeled antibodies that specifically bind the protein, peptide, or variant can be used to detect expression of the protein, peptide, or variant on a cell. See, e.g., Kim et al., J. Immunother. 20:276, 1997. In addition, Western blotting using antibodies that specifically bind the protein, peptide, or variant can be used to detect expression of the protein, peptide, or variant in lysates of a cell.

Cell types suitable for stimulating an immune response against IL-13Rα2 can be prokaryotic or eukaryotic. A number of such cells are known in the art, so an exhaustive list is not provided herein. Examples of suitable prokaryotic cells include bacterial cells such as *E. coli, B. subtilis*, and mycobacteria. Examples of suitable eukaryotic cells include plant, yeast, insect, avian, nematode (e.g., *C. elegans*), and mammalian cells (e.g., autologous cells from a human patient that are to be later reintroduced into the patient). These cells can be cultured in conventional nutrient media modified as appropriate for inducing promoters, selecting transformants, or amplifying the genes encoding the desired sequences.

Further examples of cells that can be used to stimulate an immune response against IL-13Rα2 include those that express a peptide comprising a least 7 (e.g., 7, 8, 9, 10, 11, 12, 13, 14, 15, 16, 17, 18, 19, 20 or more) contiguous amino acids of SEQ ID NO:1. For instance, an isolated cell expressing a protein having the sequence of SEQ ID NO:1 can be used. Cells into which have been introduced a purified nucleic acid that encodes a peptide comprising a least 7 contiguous amino acids of SEQ ID NO:1 might also be used.

Although any cell that can express IL-13Rα2 protein, a peptide fragment of IL-13Rα2, or a variant of the foregoing can be used to stimulate an immune response in a subject, some are preferred because of their particular antigen presentation capabilities. Examples of such cells include antigen-presenting cells (APCs) such as B lymphocytes, monocytes/macrophages, dendritic cells (DC), and other cells expressing major histocompatability complex (MHC) and/or costimulatory molecules.

As DC are known to function as particularly strong APCs able to efficiently take up, process, and present various forms of antigens to immunologically naive T cells, their use in the cell-based vaccine of the invention is particularly preferred. See, e.g., Banchereau et al., Ann. Rev. Immunology, 18:767, 2000. DC primed with a specific tumor antigen (e.g., IL-13Rα2 or peptide fragments thereof) can thus activate an anti-tumor cytotoxic T lymphocyte (CTL) response that can provide protection against and cause regression of a tumor. Several tumor-associated antigens represent tissue differentiation antigens that are poorly immunogenic due to an immune tolerance to self-antigens. Stimulation with antigen-loaded DC, however, can break tolerance to tumor-associated antigens and induce anti-tumor cytotoxic immune responses.

DC can be made to express an IL-13Rα2 protein, a peptide fragment of IL-13Rα2, or a variant thereof as described above. For example, DC can be removed from a subject, contacted with the selected antigen, and then returned to the subject to stimulate an immune response. Ex vivo protocols for DC priming with tumor-associated antigen are known in the art. See, e.g., Kumamoto et al., J. Dermatol. 28:658, 2001 and Fong et al., J. Immunol. 167:7150, 2001. Generally, DC are isolated from peripheral blood by, for example, density gradient separation, fluorescence-activated cell sorting and immunological cell separation methods. See, e.g., U.S. Pat. No. 6,194,204. The isolated DC are then cultured in media supplemented with purified antigen (e.g., IL-13Rα2) so that the DC can process the antigen for presentation to T cells. The antigen-loaded DC can be administered to a patient (e.g., injection) in a therapeutically effective amount (e.g., an amount that causes tumor regression). To enhance this response, the DC may be exposed to a cytokine (e.g., GM-CSF/IL-4) prior to administration. Tanigawa et al., J. Immunother. 26:493, 2001. In addition, specific antigen can be targeted to DC according to known methods. See, e.g., Nature Biotech. 17:253, 1999.

Those cell-based vaccines that are most effective in stimulating an immune response against IL-13Rα2 in a subject can be determined by preparing a series of different cell-based vaccine (e.g. those expressing whole antigen or specific peptide fragments of the antigen), administering a subject (or a series of genetically similar subjects) such different vaccines, and analyzing the subject(s) for the stimulation of an immune response. Those vaccines that induce the desired response can then be selected.

Anti-idiotypic Antibody Vaccines

The invention also contemplates the use of anti-idiotypic antibody vaccines to stimulate an immune response against IL-13Rα2 in a subject. In this method, anti-idiotypic antibodies are prepared that feature an internal "image" of one or more immunogenic portions of IL-13Rα2. See, e.g., U.S. Pat. Nos. 5,053,224; 5,208,146; 5,612,030; and 5,925,362. Administration of these anti-idiotypic antibodies in a vaccine composition to a subject can stimulate an immune response against the "image" of an immunogenic portion of IL-13Rα2 which cross-reacts against actual immunogenic portions of IL-13Rα2. As one example, polyclonal anti-idiotypic antibodies can be generated by immunizing a host animal with monoclonal antibodies raised against an epitope of IL-13Rα2. Methods of preparing monoclonal and polyclonal antibodies as described in more detail below.

Antibody Production

The vaccines/antigenic agents featured in the invention can be used to raise antibodies useful in the invention. Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the IL-13Rα2 proteins and peptides described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77-96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Human or humanoid antibodies that specifically bind a IL-13Rα2 protein can also be produced using known methods. For example, polyclonal antibodies can also be collected from human subjects having such antibodies in their sera, e.g., subjects administered vaccines that stimulate antibody production against IL-13Rα2. As another example, human antibodies against IL-13Rα2 protein can be made by adapting known techniques for producing human antibodies in animals such as mice. See, e.g., Fishwild, D. M. et al., Nature Biotechnology 14 (1996): 845-851; Heijnen, I. et al., Journal of Clinical Investigation 97 (1996): 331-338; Lonberg, N. et al., Nature 368 (1994): 856-859; Morrison, S. L., Nature 368 (1994): 812-813; Neuberger, M., Nature Biotechnology 14 (1996): 826; and U.S. Pat. Nos. 5,545,806; 5,569,825; 5,877,397; 5,939,598; 6,075,181; 6,091,001; 6,114,598; and 6,130,314. Humanoid antibodies against IL-13Rα2 can be made from non-human antibodies by adapting known methods such as those described in U.S. Pat. Nos. 5,530,101; 5,585,089; 5,693,761; and 5,693,762.

Once produced, polyclonal or monoclonal antibodies can be tested for specific IL-13Rα2 recognition by Western blot or immunoprecipitation analysis by standard methods, for example, as described in Ausubel et al., supra. Antibodies that specifically recognize and bind to IL-13Rα2 are useful in the invention. For example, such antibodies can be used in an immunoassay to monitor the level of IL-13Rα2 in a sample (e.g., to determine the amount of cellular expression or subcellular location of IL-13Rα2, or the presence and amount of soluble forms of IL-13Rα2 in a liquid sample).

Preferably, IL-13Rα2 protein selective antibodies of the invention are produced using fragments of the IL-13Rα2 protein that lie outside highly conserved regions and appear likely to be antigenic by criteria such as high frequency of charged residues. Cross-reactive anti-IL-13Rα2 protein antibodies are produced using a fragment of a IL-13Rα2 protein that is conserved among members of this family of proteins. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant IL-13Rα2 proteins or control proteins, such as glucocorticoid receptor, CAT, or luciferase.

Techniques described for the production of single chain antibodies (e.g., U.S. Pat. Nos. 4,946,778, 4,946,778, and 4,704,692) can be adapted to produce single chain antibodies against a IL-13Rα2 protein, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

Method of Inducing an Anti-IL-13Rα2 Immune Response in a Subject

The invention provides methods for stimulating a immune response against IL-13Rα2 in a subject having or at risk for developing a cancer having cells expressing IL-13Rα2. Such methods can be performed by (a) formulating as anti-cancer vaccine composition (as described above) outside of the subject and (b) administering the vaccine to the subject in an amount sufficient to stimulate an immune response against IL-13Rα2 in the subject.

Subjects

The compositions and methods of the invention can be utilized with any suitable subject, e.g., an animal such as a mammal (e.g., human beings, dogs, cats, goats, sheep, cows, horses, etc.). A human patient suffering or at risk for developing a cancer or other disease that has cells that overexpress IL-13Rα2 (e.g., a brain cancer such as HGG) is a particularly preferred subject.

IL-13Rα2 as a Component of a Polyvalent Vaccine

The invention also provides polyvalent vaccines that incorporate one or more of the foregoing compositions that can stimulate an immune response against IL-13Rα2 in a subject. Two general types of polyvalent vaccines are within the invention. First, a vaccine that contains more than one agent that can stimulate an immune response against IL-13Rα2 (e.g., a composition that contains 2, 3, 4, 5, 6, 7, 8, or more different peptides listed in Table I below). Second, a vaccine that contains both (a) an agent that can stimulate and immune response against IL-13Rα2 and (b) a different agent that can stimulate an immune response against a molecule other than IL-13Rα2 (e.g., another TSA or TAA).

Administering Vaccines to a Subject

The vaccine compositions of the present invention can be used in a method for stimulating an immune response against IL-13Rα2 in a subject. In this method, an vaccine composition of the invention can be administered to a subject by any method that stimulates the aforesaid immune response. The exact method selected is determined by the particular vaccine composition to administered. For parenteral administration by injection, the injection can be in situ (i.e., to a particular tissue or location on a tissue, e.g., into a tumor or lymph node), intramuscular, intravenous, intaperitoneal, or by another parenteral route. For example, for a protein/peptide based vaccine the vaccine may be administered by subcutaneous or intradermal injection. In some cases other routes can be used, e.g. intravenous injection, intraperitoneal injection, or in situ injection into target tissue.

Naked nucleic acid vaccines or expression vector vaccines may be administered by intramuscular injection. Cell-based vaccines can be introduced into an animal by any suitable method, e.g., subcutaneous injection. In addition to parenteral routes, the vaccines of the invention can also be administered by a non-parenteral route, e.g, by oral, buccal, urethral, vaginal, or rectal administration.

Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the vaccine compositions may be in powder form (e.g., lyophilized) for constitution with a suitable vehicle, for example, sterile pyrogen-free water, before use.

To facilitate delivery of the antigenic compositions (e.g., antigenic agent plus adjuvant) of the invention to an animal, the antigenic compositions can be mixed with a pharmaceutically acceptable carrier or excipient. Examples of such pharmaceutically acceptable carriers and excipients include diluents such as water, saline, citrate buffered saline, phosphate buffered saline, acetate buffered saline, and bicarbonate buffered saline; and stabilizing agents such as amino acids, alcohols, proteins (for example, serum albumin), EDTA, mannitol, sorbitol, and glycerol. To minimize the chance of infection or adverse reaction when administered to a subject, carriers and excipients are preferably sterile and pyrogen-free. USP grade carriers and excipients are particularly preferred for delivery of vaccine compositions to human subjects. The vaccine compositions can also be formulated for long-term release as a depot preparation by adding the antigenic agent to suitable polymeric or hydrophobic materials or ion exchange resins. They can also be made by preparing the vaccine composition as a sparingly soluble derivative. Depot preparations can be administered to a subject by implantation (e.g., subcutaneous or intramuscular surgical implantation) or by injection. Methods for malting the foregoing formulations are well known and can be found in, for example, *Remington's Pharmaceutical Sciences.*

Dosing

The vaccine compositions of the invention are preferably administered to a subject in an amount sufficient to stimulate an immune response against IL-13Rα2 in the subject, and not cause an overly toxic effect. Such a therapeutically effective amount can be determined as described below.

Toxicity and therapeutic efficacy of the vaccines utilized in the invention can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Vaccines that exhibit large therapeutic indices are preferred. While those that exhibit toxic side effects may be used, care should be taken to design a delivery system that minimizes the potential damage of such side effects. Data obtained from animal studies can be used in formulating a range of dosage for use in humans. The dosage of such vaccines lies preferably within a range that include an $ED_{50}$ with little or no toxicity. The dosage may vary within this range depending upon the dosage form employed and the route of administration utilized.

The vaccines of the invention can be administered to a subject using various different vaccination schedules. For example, a nucleic acid vaccine might be administered to a subject only once, while a protein/peptide-based vaccine might be administered to the subject on multiple occasions (1, 2, 3, 4, 5 or more times). For example, in an effort to stimulate a strong immune response, a first dose of a vaccine compositions of the invention may be administered to a subject at least 24 hours before a second (booster) dose is administered to the subject.

Kits

The invention also provides kits for stimulating an immune response against IL-13Rα2 in a subject. Such kits can include a container holding one or more of the antigenic agents described above in a pharmaceutically acceptable form. The antigenic agent(s) in the container can be in liquid form (e.g., as a solution) or in solid form (e.g., as a lyophilized or desiccated powder). Where, for example, the antigenic agent is a solid, the kits within the invention can further include a container holding a pharmaceutically acceptable solution (e.g., sterile saline with or without dextrose) for reconstituting the solid into a liquid suitable for injection. The kits of the invention can further include (a) one or more devices to administer the antigenic agent, e.g., a needle or syringe, a packaged alcohol pad, etc.; and/or (b) printed instructions for using the kit.

EXAMPLES

Example 1

IL-13Rα2 Mimics the Biological Features of an HGG-associated Receptor for IL-13

Normal Chinese hamster ovary (CHO) cells were transfected with a pcDNA 3.1 plasmid (Invitrogen) containing the full length open reading frame of IL-13Rα2 and positive clones were selected with geneticin. The expression of IL-13Rα2 in these clones was tested for their ability to bind $^{125}$I-labeled IL-13. Selected clones were shown to bind labeled IL-13 independently of IL-4. In addition, labeled IL-13 was displaced by IL-13.E13K, a mutant of IL-13 shown to have a greater affinity for the IL-13 binding protein on HGG than for the shared IL-13/IL-4 receptor found in a plethora of tissues under a physiological state. Furthermore, these IL-13Rα transfected CHO cells were exposed to an IL-13.E13K-PE38QQR cytotoxin, a fusion protein showing potent dose dependent cytotoxicity on HGG cells. The clones expressing the receptor were killed in direct proportion to their affinity for IL-13, but not CHO cells alone or CHO cells transfected with an empty plasmid. In neutralization experiments, an excess of IL-13 prevented the cytotoxic effect of IL-13.E13K-PE38QQR. Therefore the only way the toxin, PE38QQR, could have entered and killed the cells was through receptor-mediated endocytosis, a process directed through the IL-13 portion of the cytotoxin. Use of an IL-13.E13K/enhanced green fluorescent protein (EGFP) fusion protein confirmed that this process occurred. Thus, IL-13Rα2 was demonstrated to share properties ascribed to more restrictive, IL-4 independent, IL-13 binding sites found on HGGs in situ and in vitro.

Example 2

Identification of IL-13Rα2 as a Cancer Testis Antigen

Materials and Methods

Sources of RNA. High-grade glioma cell lines A-172 MG, U-373 MG, U-251 MG and human glioblastoma multiforme explant cells (G-48) were grown in culture in appropriate media. Total RNA was extracted from the cells using the acid-guanidium isothiocyanate-phenol -chloroform method. Poly(A)+ RNA was further isolated using the Mini-oligo(dT) Cellulose Spin Column Kit (5 prime-3 prime Inc., Boulder, Colo.). 2 μg of Poly (A)+ RNA was electrophoresed on a 1% agarose formaldehyde gel, transferred to 0.45 μm magna charge nylon (MST, Westborough, Mass.) and UV-crosslinked (Stratagene, La Jolla, Calif.). RNA-blotted membranes were also purchased from Clontech (Palo Alto, Calif.). Two Multiple Tissue Expression (MTETM) Blots (cat # 7770-1 and 7775-1were analyzed to determine the tissue distribution of the IL-13 binding proteins. Two sets of Human Brain Multiple Tissue Northern (MTNTM) Blots (cat # 7755-1 and 7769-1) were assayed to confirm the true presence of the transcripts. In addition, two Human Tissue Northern (MTNTM) Blots (cat # 7759-1 and 7760-1) were analyzed to verify the tissue distribution of the IL-13Rα2 transcript.

cDNA Probes. cDNA probes were generated either by PCR (IL-13Rα2 and IL-13Rα1) or by restriction digest (IL-4Rα=p140). cDNA containing human IL-13Rα2 was provided by Dr. Pascual Ferrara of Sanofi Recherche. cDNA containing human IL-13Rα1 (and also 93 bases of murine IL-13) was provided by Dr. Douglas J. Hilton of The Walter and Eliza Hall Institute of Medical Research. Plasmid pHuIL-4R/ID was used to obtain a fragment of IL-4Rα by the restriction digest. The fragments were electrophoresed on a 1% agarose gel, excised from the gel and purified using QIAquick Gel Extraction Kit (Qiagen Inc., Valencia, Calif.). Actin cDNA was purchased from Clontech Labs.

The primers for human IL-13Rα2 were as follows:

```
                                              (SEQ ID NO: 3)
forward 5'-AAGATTTGGAAGCTTATGGCTTTCGTTTGC-3'

(SEQ ID NO: 4)
reverse 5'-TCCCTCGAAGCTTCATGTATCACAGAAAAA-3'
```

The primers for human IL-13Rα1 were as follows:

```
                                         (SEQ ID NO: 5)
    forward 5'-ATTATTAAGCTTATGGAGTGGCCGGCG-3'

(SEQ ID NO: 6)
    reverse 5'-TAACCGGAAGCTTCACTGAGAGGCTTT-3'
```

Northern Blot Analysis. Membranes were pre-hybridized overnight at 42° C. in a solution consisting of 50% formamide, 5×SSC, 50 mM sodium phosphate, 5×Denhardt's, 50 µg/ml sheared salmon sperm DNA, and 1% SDS. Membranes were subsequently hybridized overnight at 42° C. in the same solution with the addition of full length cDNA probes labeled by random priming (Life Technologies, Rockville, Md.) with $^{32}$P-dCTP using 1-2×10$^6$ cpm/ml. Following hybridization, the membranes were washed with 2×SSC/0.2% SDS at 42° C. for 20 minutes followed by two washes with 1×SSC/0.1% SDS at 42° C. for 20 minutes each. The membranes were exposed to autoradioraphic film X-OMAT AR (Eastman Kodak Co., Rochester, N.Y.) and placed at −80° C. for 1, 3 and 14 days. The membranes were subsequently stripped and re-probed up to three more times. The membranes were probed first with IL-13Rα2, followed by IL-13Rα1, IL-4Rα=p140, and actin. Films were scanned on a transparency scanner at a pixel size of 88×88 micron (Molecular Dynamics, Sunnyvale, Calif.). The images were compiled in Paint Shop Pro V 5.0 (Jasc software Inc., Eden Prairie, Minn.).

Results

Northern blot analysis of transcripts for IL-13Rα2 in normal organs. To explore the expression of IL-13Rα2, an extensive examination of the presence of transcripts for this protein among multiple normal tissues, including 20 discrete regions of the CNS and a variety of normal peripheral organs was performed. All Northern blots using same membranes were performed with respective labeled cDNAs in the following order: IL-13Rα2, IL-13Rα1, IL-4α and β-actin. This assured that the levels of transcripts for IL-13Rα2 were not underestimated due to the usage of membranes with mRNA. Both the dot-blot analyses (not shown) and the electrophoretically separated transcripts for IL-13Rα2 (FIG. 4, panels I-IV) demonstrated mostly undetectable, or very weak signals in few cases, of IL-13Rα2 transcripts in the organs studied, even after 2-week of film exposure. The first dot blot performed, however, surprisingly showed an unusually high density of labeling with IL-13Rα2 cDNA probe to transcripts derived from testis. This was also found using another Northern blot membrane. A few other organs had transcripts that hybridized to the IL-13Rα2 cDNA (aorta, liver, and pituitary gland). The density of labeling in the dot blots was much lower than in the testis blot. Of importance, there was no evidence for the presence of significant IL-13Rα2 expression in the CNS.

To confirm these findings made using dot blot analysis, additional blots were performed using electrophoretically separated mRNAs. Again, the discrete regions of normal human brain did not produce clear-cut hybridization signals (FIG. 4, panels I and II). On the other hand, the only organ with prominent hybridization band corresponding to the mRNA of 1.5 kb was seen in testis (FIG. 4, panel III). Poorly detectable signals were seen in placenta, liver, and kidney (FIG. 4, panel IV). Thus, among normal tissues, testes was the only one that prominently expressed IL-13Rα2. No transcripts for IL-13Rα2 were readily detected in the CNS.

Figure 5:
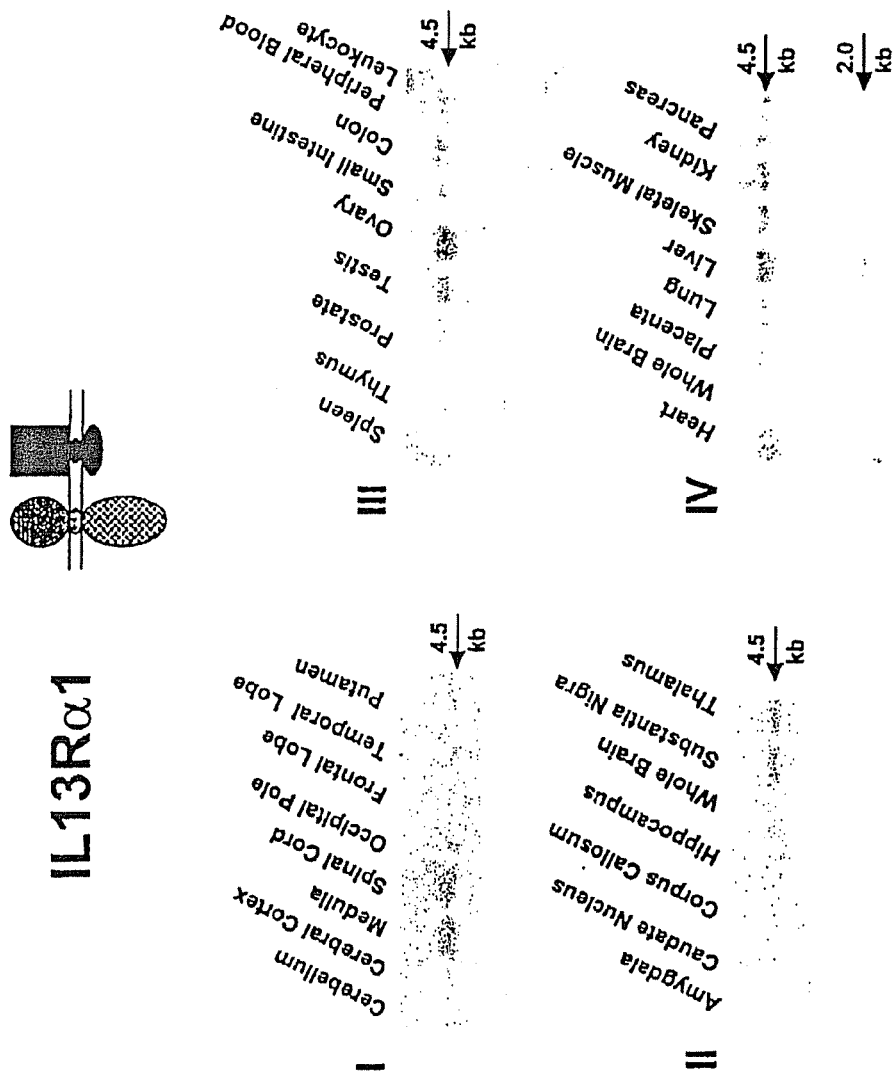
FIG. 5 is a Northern blot analysis of human IL-13Rα2 transcripts (closed figure) in series of CNS (panels I and II) and peripheral tissues (panels III and IV). The migration position of mRNA is shown in kilobases. Films were exposed for 2 weeks except for membranes shown in panels III and IV, which were exposed for 3 days.

Northern blot analysis of transcripts for IL-13Rα1 in normal tissues. The expression of IL-13Rα1, a component of a heterodimeric form of IL-13 receptor that is shared with IL-4, IL-13/4 receptor was examined in a variety of normal human tissues (FIG. 5) by either dot-blot analyses (not shown) or blots of electrophoretically separated transcripts (FIG. 5, panels I-IV). The results unequivocally demonstrated that IL-13Rα1 was expressed in a variety of the organs, including CNS tissue from medulla, spinal cord, substantia nigra, thalamus, and corpus callosum. Size fractionated mRNAs confirmed the many positive signals seen in dot blots with the strongest signals observed in ovary, heart, liver and lung (FIG. 5, panels III and IV, respectively). Of interest, liver showed two hybridized species of mRNA: one of 4.5 kb and the other of 2.0 kb, as an example of a normal organ with doublet of positive signals of different sizes. In summary, discrete regions of normal human brain did produce clear-cut positive hybridization signals for IL-13Rα1 (FIG. 5, panels I and II). In addition, many vital peripheral organs exhibited hybridization bands corresponding to the mRNA of 4.5-4.65 kb (FIG. 5, panels II and IV).

Figure 6:
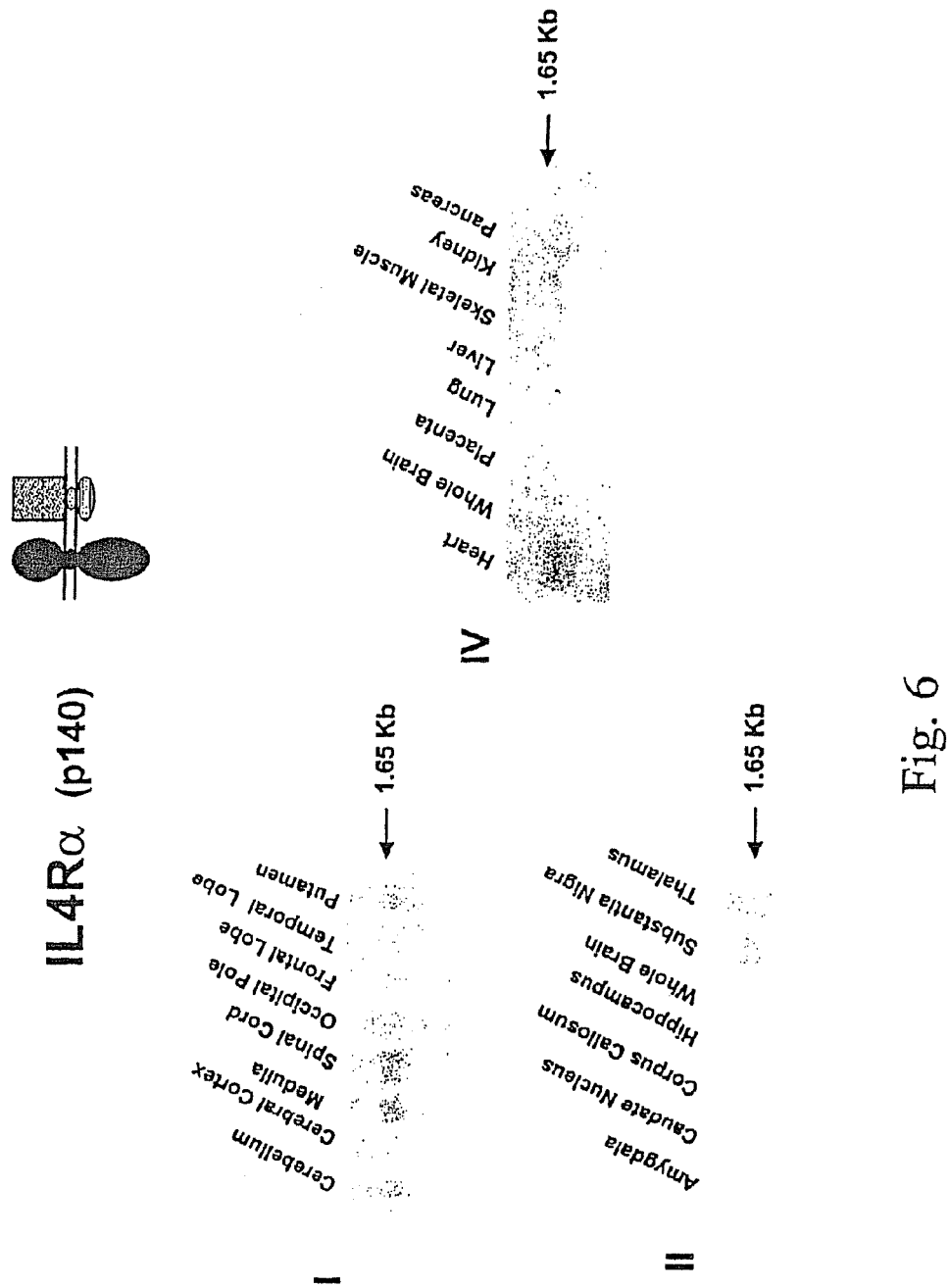
FIG. 6 is a Northern blot analysis of human 140-kDa IL-4R α-chain transcripts (closed figure) in series of CNS (panels I and II) and peripheral tissues (panel IV). The migration position of mRNA is shown in kilobases. Films were exposed for 2 weeks.

Gene expression analysis of IL-4Rα in normal tissues. In addition to IL-13Rα1, IL-4Rα is another component of a heterodimeric form of IL-13 receptor that is shared with IL-4, i.e., the shared IL-13/4 receptor. Thus, whether the distribution of IL-4Rα gene expression corresponded to that of IL-13Rα1 was analyzed. All Northern blot analysis membranes used in this study demonstrated enriched content of the IL-4Rα transcripts in a variety of tissues (FIG. 6, panels I, II, and IV). The presence of the transcripts within the CNS was most evident, as it was for IL-13Rα1, in medulla, spinal cord, substantia nigra and thalamus (FIG. 6, panels I and II). Among normal peripheral organs, liver, lung, kidney, intestinal tract, spleen, stomach, and testis demonstrated gene expression of IL-4Rα, which was generally similar to that seen with IL-13Rα1 (not shown). Thus, discrete regions of normal human brain contain transcripts for both IL-13Rα1 and IL-4Rα, a complete heterodimer of the shared IL-13/4 receptor. Furthermore, several vital peripheral organs contained the two subunits of the IL-13/4 receptor, including heart, liver, lung and intestinal tract.

Figure 7:
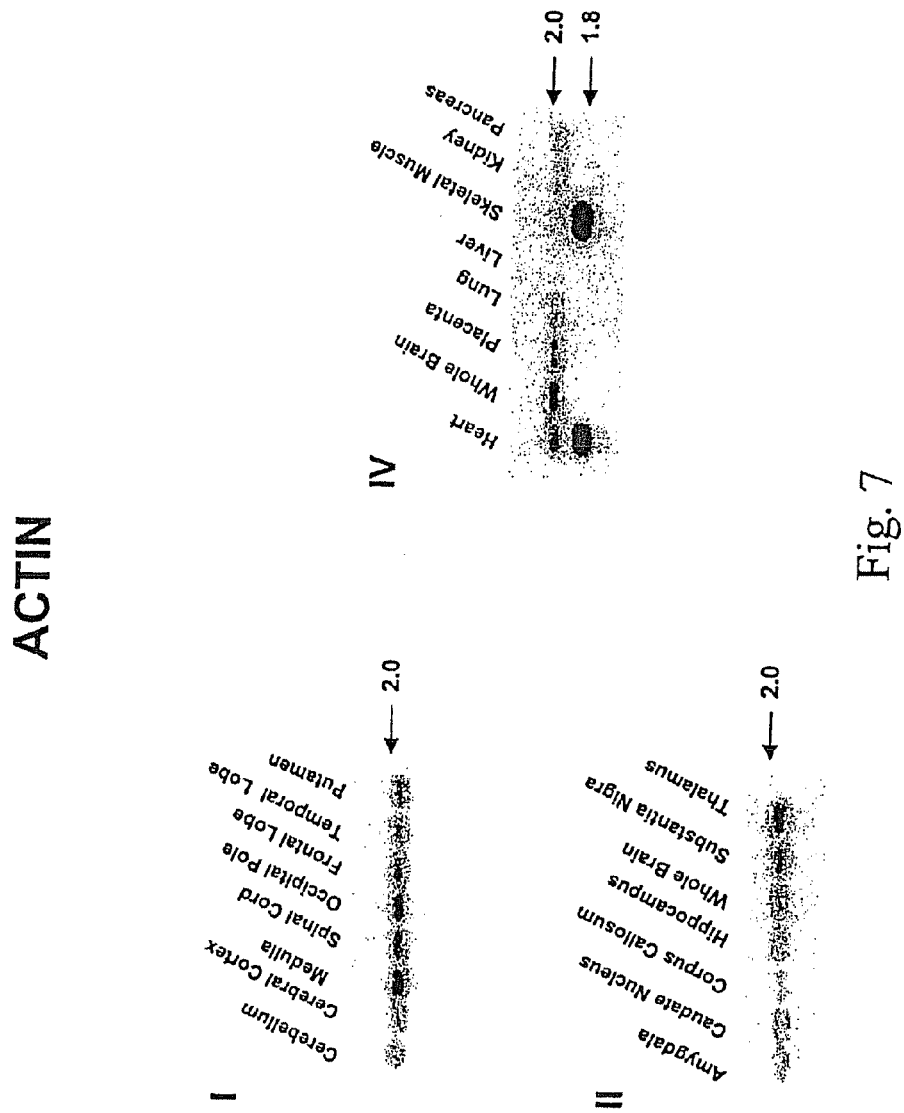
FIG. 7 is a Northern blot analysis of human β-actin transcripts in CNS (panels I and II) and peripheral tissues (panel IV). The migration position of mRNA is shown in kilobases. Films were exposed for 1-3 hours.

Control hybridization of β-actin. All membranes used for Northern blot analysis of IL-13 receptors transcripts were also hybridized with a cDNA probe for a house-keeping gene, β-actin (FIG. 7; dot blots and panel III not shown). The intensity of the signals for β-actin was usually in accordance with the amount of mRNA present on the membranes, as estimated by the manufacturer.

Figure 8:
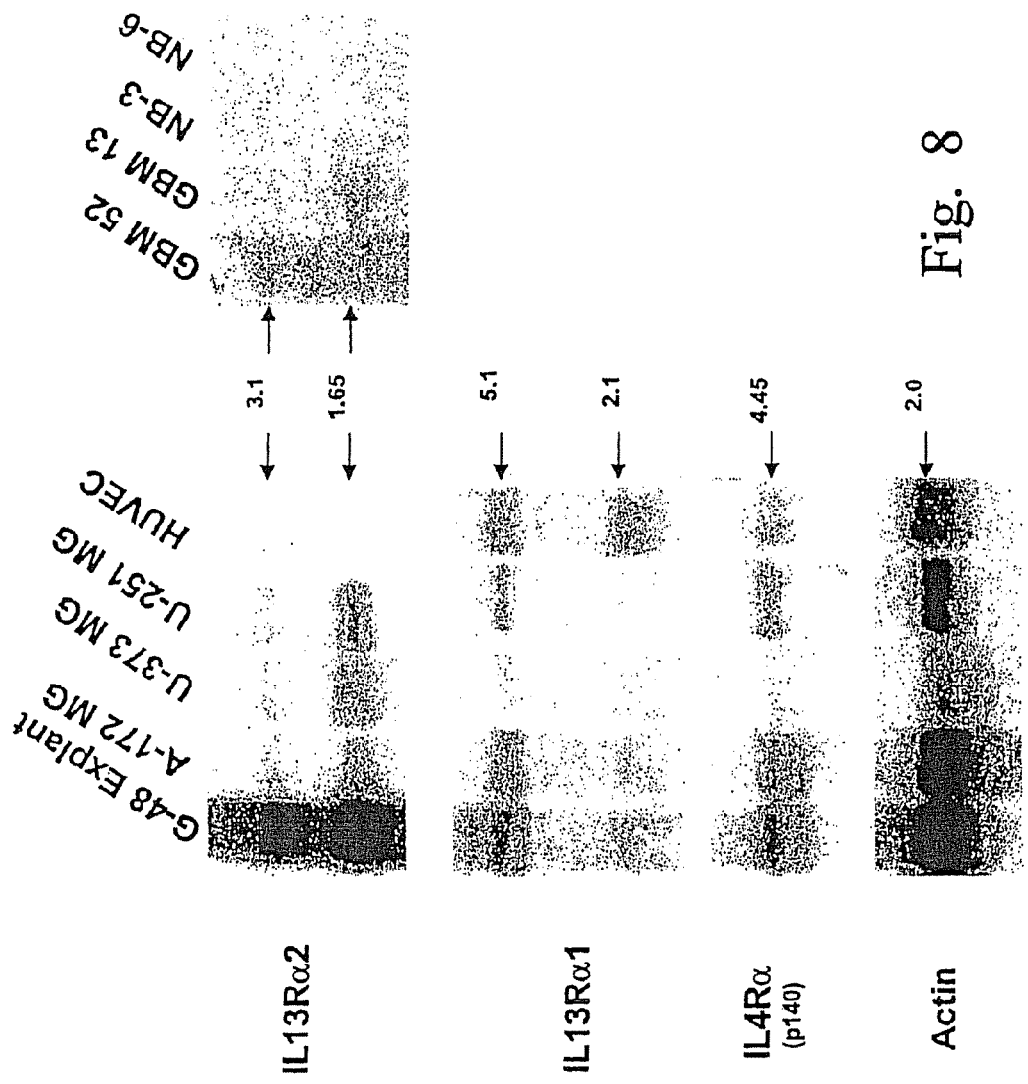
FIG. 8 is a Northern blot analysis of transcripts of different IL-13 receptors in malignant glioma cells (G-48, A-172 MG, U-373 MG, and U-251 MG), normal human umbilical vein endothelial cells (HUVEC) and in surgical specimens of GBM and normal human brain. The migration position of mRNA is shown in kilobases. Films were exposed for 2 weeks, except for actin (1 hr).

Gene expression of IL-13 receptors in cells; Gene expression of the two IL-13 receptors was also examined in malignant and normal cells (FIG. 8). Transcripts for IL-13Rα2, IL-13Rα1, IL-4Rα and β-actin were examined in serial hybridization assays. Isolated explant cells of HGG (G-48) as well as human malignant glioma established cell lines (A-172 MG, U-373 MG, and U-251 MG) demonstrated intense signals for IL-13Rα2 (FIG. 8). On the other hand, the transcripts for the elements of the shared IL-13/4 receptor, IL-13Rα1 and IL-4Rα, were found at lower levels when compared with that for IL-13Rα2<FIG. 8). A-172 MG cells appeared to be the most enriched in the components of the IL-13/4 receptor heterodimer. Of interest, two species of different sizes of the transcripts for both IL-13Rα2 and IL-13Rα1 were seen in cells (FIG. 8). In a control assay, human umbilical vein endothelial cells (HUVEC) showed the presence of transcripts for IL-13Rα1 and IL-4Rα, but not those for IL-13Rα2 (FIG. 8). In summary, gene expression of IL-13Rα2 was detected in two specimens of HGG (FIG. 8, HGG 13 and HGG 52), but not in two normal brain specimens (FIG. 8, NB 3 and NB 6). However, the transcripts for IL-13Rα1 were found in all of

Example 3

Representative Immunogenic Peptides of IL-13Rα2

Table I presents a list of IL-13Rα2 peptides that might be used to stimulate an immune response against IL-13Rα2 in a subject. The listed peptides were obtained using a computer program provided by the Ludwig Institute For Cancer Research (Lausanne, Switzerland). This program provided the best (at high stringency) fit of predicted immunogenic peptides that bind specific classes of MHC molecules (i.e., the various alleles of human MHC Class I indicated in Table I). The peptides indicated with the "*" are those that should bind under high stringency. The skilled artisan could produce these peptides as described herein (e.g., by automated peptide synthesis) and use each in a vaccine preparation that would be administered to a variety of test subjects (e.g. those with different MHC types) as also described herein. The immune response stimulated by each of these peptides in the subjects could then be assessed, so that those that stimulate the desired immune responses in particular test subjects could be identified.

TABLE I

Binding peptides prediction:

| Allele | Peptide | Position | Score | t½ |
|---|---|---|---|---|
| A1 | IVDP-GYLGY | 16-24 | 7.120 | 1236.45043346563 |
| A1 | LLDTNYNLFY | 140-149 | 4.820 | 123.965090779824 |
| A_0201 | YLYLQWQPPL | *24-33 | 5.760 | 317.34832891785 |
| A_0201 | YLQWQPPLSL | *26-35 | 4.600 | 99.4843156419338 |
| A_0201 | LQWQ-PPLSL | 27-35 | 3.430 | 30.876642749677 |
| A_0201 | SLDHFKECTV | 34-43 | 3.330 | 27.9383417032365 |
| A_0201 | NLHYKDGFDL | *64-73 | 4.830 | 125.210960654765 |
| A_0201 | WQCT-NGSEV | 87-95 | 3.490 | 32.7859477062319 |
| A_0201 | CVYY-NWQYL | *121-129 | 4.020 | 55.7011058267956 |
| A_0201 | YLLCSWKPGI | *128-137 | 5.190 | 179.468552931832 |
| A_0201 | VLLD-TNYNL | *139-147 | 6.320 | 555.572992451403 |
| A_0201 | NLFY-WYEGL | *146-154 | 4.080 | 59.1454698498823 |
| A_0201 | GLDH-ALQCV | *153-161 | 4.160 | 64.0715225999366 |
| A_0201 | NIGC-RFPYL | 170-178 | 3.420 | 30.5694150210502 |
| A_0201 | FQLQNIVKPL | *206-215 | 4.450 | 85.6269440022006 |
| A_0201 | QLQN-IVKPL | *207-215 | 3.900 | 49.4024491055302 |
| A_0201 | NIVK-PLPPV | 210-218 | 3.090 | 21.9770779757634 |
| A_0201 | YLTFTRESSC | 219-228 | 3.140 | 23.1038668587222 |
| A_0201 | QLCFVVRSKV | *279-288 | 4.250 | 70.1054123466879 |
| A_0205 | IVDPGYLGYL | 16-25 | 3.120 | 22.6463796431754 |
| A_0205 | YLYLQWQPPL | *24-33 | 4.140 | 62.8028214492017 |
| A_0205 | LQWQ-PPLSL | 27-35 | 3.350 | 28.5027336437673 |
| A_0205 | LQWQ-PPLSL | 26-35 | 3.040 | 20.9052432350928 |
| A_0205 | CVYY-NWQYL | *121-129 | 4.430 | 83.9314169102688 |
| A_0205 | VLLD-TNYNL | *139-147 | 4.670 | 106.697742432451 |
| A_0205 | VLLD-TNYNL | *138-147 | 3.740 | 42.0979901649969 |
| A_0205 | NLFY-WYEGL | 146-154 | 3.040 | 20.9052432350928 |
| A_0205 | FQLQNIVKPL | *206-215 | 4.610 | 100.484149636389 |
| A3 | LLDTNYNLFY | 140-149 | 3.190 | 24.2884274430946 |
| A3 | ALQC-VDYIK | 157-165 | 4.520 | 91.8355979781567 |
| A3 | GIWS-EWSDK | 296-304 | 3.410 | 30.2652442594001 |
| A24 | DFEIVDPGYL | 13-22 | 3.410 | 30.2652442594001 |
| A24 | LYLQ-WQPPL | *25-33 | 5.710 | 301.87106828279 |
| A24 | EYEL-KYRNI | *44-52 | 4.320 | 75.1886282920231 |
| A24 | TYWI-SPQGI | *103-111 | 4.090 | 59.7398917041452 |
| A24 | VYYN-WQYLL | *122-130 | 5.300 | 200.336809974792 |
| A24 | WYEG-LDHAL | *150-158 | 5.890 | 361.405284372286 |
| A24 | DYIKADGQNI | *162-171 | 4.500 | 90.0171313005218 |
| A24 | SYFTFQLQNI | *202-211 | 4.090 | 59.7398917041452 |
| A | DLSK-KTLLR | 311-319 | 3.300 | 27.1126389206579 |
| A68.1 | TVEY-ELKYR | *42-50 | 5.300 | 200.336809974792 |
| A68.1 | TVEY-ELKYR | *41-50 | 4.600 | 99.4843156419338 |
| A68.1 | ETWK-TIITK | *55-63 | 4.500 | 90.0171313005218 |
| A68.1 | CVNG-SSENK | *189-197 | 4.790 | 120.301368663215 |
| A68.1 | FTFQLQNIVK | *204-213 | 4.090 | 59.7398917041452 |
| A68.1 | FTRESSCEIK | 222-231 | 3.400 | 29.964100047397 |
| A68.1 | ESSC-EIKLK | 225-233 | 3.300 | 27.1126389206579 |
| A68.1 | TVENETYTLK | *263-272 | 4.790 | 120.301368663215 |
| A68.1 | YTLKTTNETR | *269-278 | 4.600 | 99.4843156419338 |
| A68.1 | ETRQLCFVVR | *276-285 | 5.010 | 149.904736149047 |
| B7 | DPGYLGYLYL | 18-27 | 4.390 | 80.640418980477 |
| B7 | CVYY-NWQYL | 121-129 | 3.000 | 20.0855369231877 |
| B7 | GVLLDTNYNL | 138-147 | 3.000 | 20.0855369231877 |
| B7 | IVKPLPPVYL | 211-220 | 3.410 | 30.2652442594001 |
| B7 | EIRE-DDTTL | 251-259 | 3.690 | 40.0448469572867 |
| B8_8mer | EAKIHTLL | 78-85 | 3.470 | 32.1367424447532 |
| B8_8mer | EIKLKWSI | 229-236 | 3.690 | 40.0448469572867 |
| B8_8mer | VVRSKVNI | 283-290 | 3.000 | 20.0855369231877 |
| B14 | QNIGCRFPYL | 169-178 | 3.400 | 29.964100047397 |

TABLE I-continued

Binding peptides prediction:

| Allele | Peptide | Position | Score | t½ |
|---|---|---|---|---|
| B14 | IRSSYFTFQL | 199-208 | 3.000 | 20.0855369231877 |
| B_2702 | LQWQ-PPLSL | 27-35 | 3.410 | 30.2652442594001 |
| B_2702 | WQPPLSLDHF | 29-38 | 3.000 | 20.0855369231877 |
| B_2702 | YRNI-GSETW | 49-57 | 4.610 | 100.484149636389 |
| B_2702 | VQSSWAETTY | 95-104 | 3.000 | 20.0855369231877 |
| B_2702 | VQDM-DCVYY | 116-124 | 3.000 | 20.0855369231877 |
| B_2702 | GQNIGCRFPY | 168-177 | 3.000 | 20.0855369231877 |
| B_2702 | CRFP-YLEAS | 173-181 | 3.920 | 50.4004447780655 |
| B_2702 | IRSSYFTFQL | 199-208 | 4.100 | 60.340287597362 |
| B_2702 | TRESSCEIKL | 223-232 | 4.100 | 60.340287597362 |
| B_2702 | ARCFDYEIEI | 243-252 | 4.100 | 60.340287597362 |
| B_2702 | IRED-DTTLV | 252-260 | 3.000 | 20.0855369231877 |
| B_2702 | VRSK-VNIYC | 284-292 | 3.000 | 20.0855369231877 |
| B_2705 | FEIV-DPGYL | 14-22 | 3.400 | 29.964100047397 |
| B_2705 | YLYLQWQPPL | 24-33 | 5.010 | 149.904736149047 |
| B_2705 | LQWQ-PPLSL | 27-35 | 6.910 | 1002.24724229025 |
| B_2705 | LQWQ-PPLSL | 26-35 | 3.400 | 29.964100047397 |
| B_2705 | WQPPLSLDHF | 29-38 | 4.610 | 100.484149636389 |
| B_2705 | KECT-VEYEL | 39-47 | 4.500 | 90.0171313005218 |
| B_2705 | YRNIGSETWK | 49-58 | 7.600 | 1998.19589510412 |
| B_2705 | RNIG-SETWK | 50-58 | 4.090 | 59.7398917041452 |
| B_2705 | SETWKTIITK | 54-63 | 3.400 | 29.964100047397 |
| B_2705 | KNLH-YKDGF | 63-71 | 3.400 | 29.964100047397 |
| B_2705 | NLHYKDGFDL | 64-73 | 3.400 | 29.964100047397 |
| B_2705 | IEAK-IHTLL | 77-85 | 3.400 | 29.964100047397 |
| B_2705 | WQCT-NGSEV | 87-95 | 4.100 | 60.340287597362 |
| B_2705 | VQSSWAETTY | 95-104 | 4.610 | 100.484149636389 |
| B_2705 | VQDM-DCVYY | 116-124 | 4.610 | 100.484149636389 |
| B_2705 | CVYY-NWQYL | 121-129 | 3.910 | 49.8989519734079 |
| B_2705 | WQYL-LCSWK | 126-134 | 6.910 | 1002.24724229025 |
| B_2705 | CSWKPGIGVL | 131-140 | 3.910 | 49.8989519734079 |
| B_2705 | VLLD-TNYNL | 139-147 | 3.400 | 29.964100047397 |
| B_2705 | TNYN-LFYWY | 143-151 | 3.910 | 49.8989519734079 |
| B_2705 | NLFY-WYEGL | 146-154 | 5.010 | 149.904736149047 |
| B_2705 | ALQC-VDYIK | 157-165 | 3.400 | 29.964100047397 |
| B_2705 | LQCV-DYIKA | 158-166 | 3.000 | 20.0855369231877 |
| B_2705 | GQNIGCRFPY | 168-177 | 4.610 | 100.484149636389 |
| B_2705 | CRFP-YLEAS | 173-181 | 6.910 | 1002.24724229025 |
| B_2705 | FPYLEASDYK | 175-184 | 3.910 | 49.8989519734079 |
| B_2705 | IRSSYFTFQL | 199-208 | 7.600 | 1998.19589510412 |
| B_2705 | RSSY-FTFQL | 200-208 | 3.400 | 29.964100047397 |
| B_2705 | FTFQLQNIVK | 204-213 | 3.910 | 49.8989519734079 |
| B_2705 | FQLQNIVKPL | 206-215 | 4.100 | 60.340287597362 |
| B_2705 | TRES-SCEIK | 223-231 | 7.600 | 1998.19589510412 |
| B_2705 | RESS-CEIKL | 224-232 | 4.500 | 90.0171313005218 |
| B_2705 | ARCFDYEIEI | 243-252 | 6.400 | 601.845037872082 |
| B_2705 | RCFDYEIEIR | 244-253 | 4.320 | 75.1886282920231 |
| B_2705 | IRED-DTTLV | 252-260 | 6.400 | 601.845037872082 |
| B_2705 | IEIREDDTTL | 250-259 | 3.400 | 29.964100047397 |
| B_2705 | VENE-TYTLK | 264-272 | 3.400 | 29.964100047397 |
| B_2705 | TRQL-CFVVR | 277-285 | 6.910 | 1002.24724229025 |
| B_2705 | RQLCFVVRSK | 278-287 | 5.200 | 181.272241875151 |
| B_2705 | VRSK-VNIYC | 284-292 | 5.300 | 200.336809974792 |
| B_2705 | GIWS-EWSDS | 296-304 | 3.910 | 49.8989519734079 |
| B_2705 | KQCW-EGEDL | 304-312 | 6.400 | 601.845037872082 |
| B_2705 | QCWEGEDLSK | 305-314 | 3.910 | 49.8989519734079 |
| B_2705 | WEGE-DLSKK | 307-315 | 3.400 | 29.964100047397 |
| B_2705 | GEDLSKKTLL | 309-318 | 3.400 | 29.964100047397 |
| B_3501 | DPGY-LGYLY | 18-26 | 3.700 | 40.4473043600674 |
| B_3501 | QPPL-SLDHF | 30-38 | 3.000 | 20.0855369231877 |
| B_3501 | FPYL-EASDY | 175-183 | 4.110 | 60.9467175696222 |
| B_3501 | KPIRSSYFTF | 197-206 | 3.690 | 40.0448469572867 |
| B_3501 | KPLPPVYLTF | 213-222 | 3.690 | 40.0448469572867 |
| B_3501 | GPIPARCFDY | 239-248 | 3.700 | 40.4473043600674 |
| B3501_8mer | DPGYLGYL | 18-25 | 3.000 | 20.0855369231877 |
| B3501_8mer | KPGIGVLL | 134-141 | 3.690 | 40.0448469572867 |
| B3501_8mer | KPIRSSYF | 197-204 | 3.690 | 40.0448469572867 |
| B3501_8mer | KPLPPVYL | 213-220 | 3.690 | 40.0448469572867 |
| B3501_8mer | LPPVYLTF | 215-222 | 3.000 | 20.0855369231877 |
| B3501_8mer | GPIPARCF | 239-246 | 3.000 | 20.0855369231877 |
| B3501_8mer | IPARCFDY | 241-248 | 3.700 | 40.4473043600674 |
| B_3701 | VDPG-YLGYL | 17-25 | 3.690 | 40.0448469572867 |
| B_3701 | KDGFDLNKGI | 68-77 | 3.690 | 40.04484695272867 |
| B_3701 | IEAK-IHTLL | 77-85 | 4.320 | 75.1886282920231 |
| B_3701 | LDTN-YNLFY | 141-149 | 3.690 | 40.0448469572867 |
| B_3701 | EDLS-KKTLL | 310-318 | 5.300 | 200.336809974792 |

TABLE I-continued

Binding peptides prediction:

| Allele | Peptide | Position | Score | t½ |
|---|---|---|---|---|
| B_3701 | EDLS-KKTLL | 309-318 | 3.910 | 49.8989519734079 |
| B | LHYK-DGFDL | 65-73 | 3.400 | 29.964100047397 |
| B_3901 | LHYK-DGFDL | 65-73 | 5.190 | 179.468552931832 |
| B_3901 | DHALQCVDYI | 155-164 | 3.810 | 45.1504388663187 |
| B_3901 | TRESSCEIKL | 223-232 | 3.120 | 22.6463796431754 |
| B_3901 | IRED-DTTLV | 252-260 | 3.400 | 29.964100047397 |
| B3901_8mer | DHFKECTV | 36-43 | 4.090 | 59.7398917041452 |
| B3901_8mer | IREDDTTL | 252-259 | 4.500 | 90.0171313005218 |
| B_3902 | LQWQ-PPLSL | 27-35 | 3.000 | 20.0855369231877 |
| B_3902 | FKECTVEYEL | 38-47 | 3.180 | 24.0467535520645 |
| B_3902 | WKTI-ITKNEL | 57-65 | 3.180 | 24.0467535520645 |
| B_3902 | WKPG-IGVLL | 133-141 | 3.180 | 24.0467535520645 |
| B_3902 | FQLQNIVKPL | 206-215 | 3.180 | 24.0467535520645 |
| B_3902 | VKPL-PPVYL | 212-220 | 3.000 | 20.0855369231877 |
| B_3902 | IKLK-WSIPL | 230-238 | 3.180 | 24.0467535520645 |
| B_3902 | LKTTNETRQL | 271-280 | 3.000 | 20.0855369231877 |
| B_3902 | KQCW-EGEDL | 304-312 | 3.000 | 20.0855369231877 |
| B_3902 | DKQCWEGEDLY | 303-312 | 3.000 | 20.0855369231877 |
| B40 | FEIV-DPGYL | 14-22 | 4.390 | 80.640418980477 |
| B40 | KECT-VEYEL | 39-47 | 3.000 | 20.0855369231877 |
| B40 | IEAK-IHTLL | 77-85 | 3.690 | 40.0448469572867 |
| B40 | RESS-CEIKL | 224-232 | 3.000 | 20.0855369231877 |
| B40 | IEIREDDTTL | 250-259 | 4.390 | 80.640418980477 |
| B40 | SEWS-DKQCW | 299-307 | 3.690 | 40.0448469572867 |
| B40 | GEDL-SKKTL | 309-317 | 3.000 | 20.0855369231877 |
| B_4403 | QDFEIVDPGY | 12-21 | 3.120 | 22.6463796431754 |
| B_4403 | FEIV-DPGYL | 14-22 | 3.000 | 20.0855369231877 |
| B_4403 | VDPGYLGYLY | 17-26 | 3.210 | 22.6463796431754 |
| B_4403 | KTIITKNLHY | 58-67 | 3.530 | 34.1239676147544 |
| B_4403 | QNIG-CRFPY | 169-177 | 3.530 | 34.1239676147544 |
| B-4403 | LEASDYKDFY | 178-187 | 5.480 | 239.846707374255 |
| B_4403 | SENKPIRSSY | 194-203 | 5.480 | 239.846707374255 |
| B_4403 | CEIK-LKWSI | 228-236 | 3.000 | 20.0855369231877 |
| B_4403 | GPIPARCFDY | 239-248 | 3.810 | 45.1504388663187 |
| B_4403 | YEIEIREDDT | 248-257 | 3.000 | 20.0855369231877 |
| B_4403 | IEIREDDTTL | 250-259 | 3.410 | 30.2652442594001 |
| B_4403 | SEWS-DKQCW | 299-307 | 3.180 | 24.0467535520645 |
| B_5101 | NPPQ-DFEIV | 9-17 | 5.410 | 223.631587680546 |
| B_5101 | DPGYLGYLYL | 18-27 | 5.400 | 221.406416204187 |
| B_5101 | IGSE-TWKTI | 52-60 | 5.050 | 156.022464486395 |
| B_5101 | DGFD-LNKGI | 69-77 | 6.070 | 432.680681574476 |
| B_5101 | SPQGIPETKV | 107-116 | 5.410 | 223.631587680546 |
| B_5101 | IPET-KVQDM | 111-119 | 3.770 | 43.3800648358516 |
| B_5101 | EGLDHALQCV | 152-161 | 4.790 | 120.3013686632215 |
| B_5101 | HALQ-CVDYI | 156-164 | 5.300 | 200.336809974792 |
| B_5101 | EASDYKDFYI | 179-188 | 6.090 | 441.421411145971 |
| B_5101 | NGSS-ENKPI | 191-199 | 4.590 | 98.4944301619463 |
| B_5101 | IPARCFDYEI | 241-250 | 6.260 | 523.218940108001 |
| B_5101 | PARC-FDYEI | 242-250 | 3.000 | 20.0855369231877 |
| B_5101 | EGEDLSKKTL | 308-317 | 4.190 | 66.02279096040990 |
| B5101_8mer | NPPQDFEI | 9-16 | 6.100 | 445.857770082517 |
| B5101_8mer | PPQDFEIV | 10-17 | 3.110 | 22.4210444007463 |
| B5101_8mer | DPGYLGYL | 18-25 | 5.300 | 200.336809974792 |
| B5101_8mer | EAKIHTLL | 78-85 | 4.700 | 109.947172452124 |
| B5101_8mer | WAETTYWI | 99-106 | 5.400 | 221.406416204187 |
| B5101_8mer | QGIPETKV | 109-116 | 3.800 | 44.7011844933008 |
| B5101_8mer | KPGIGVLL | 134-141 | 4.120 | 61.5592422644285 |
| B5101_8mer | IGCRFPYL | 171-178 | 3.260 | 26.0495371425183 |
| B5101_8mer | KPLPPVYL | 213-220 | 3.920 | 50.4004447780655 |
| B_5102 | NPPQ-DFEIV | 9-7 | 5.510 | 247.151127067624 |
| B_5102 | DPGYLGYLYL | 18-27 | 4.810 | 122.731617517265 |
| B_5102 | IGSE-TWKTI | 52-60 | 4.790 | 120.301368663215 |
| B_5102 | DGFD-LNKGI | 69-77 | 6.200 | 592.749041093256 |
| B_5102 | KGIEAKIHTL | 75-84 | 4.400 | 81.4508686649681 |
| B_5102 | LPWQ-CTNGS | 85-93 | 3.430 | 30.876642749677 |
| B_5102 | SSWAETTYWI | 97-106 | 3.200 | 24.5325301971094 |
| B_5102 | TYWI-SPQGI | 103-111 | 3.100 | 22.1979512814416 |
| B_5102 | TTYWISPOGI | 102-111 | 3.100 | 22.1979512814416 |
| B_5102 | SPQGIPETKV | 107-116 | 6.100 | 445.857770082517 |
| B_5102 | YLLCSWKPGI | 128-137 | 3.180 | 24.0467535520645 |
| B_5102 | EGLDHALQCV | 152-161 | 4.900 | 134.289779684936 |
| B_5102 | HALQ-CVDYI | 156-164 | 6.600 | 735.095189241973 |
| B_5102 | FPYL-EASDY | 175-183 | 3.510 | 33.4482677839449 |
| B_5102 | EASDYKDFYI | 179-188 | 5.400 | 221.406416204187 |
| B_5102 | NGSS-ENKPI | 191-199 | 4.590 | 98.4944301619463 |
| B_5102 | KPIR-SSYFT | 197-205 | 3.510 | 33.4482677839449 |

TABLE I-continued

| Binding peptides prediction: | | | | |
|---|---|---|---|---|
| Allele | Peptide | Position | Score | t½ |
| B_5102 | SYFTFQLQNI | 202-211 | 3.300 | 27.1126389206579 |
| B_5102 | FTFQ-LQNIV | 204-212 | 3.200 | 24.5325301971094 |
| B_5102 | KPLP-PVYLT | 213-221 | 3.410 | 30.2652442594001 |
| B_5102 | IPLGPIPARC | 236-245 | 4.200 | 66.6863310409252 |
| B_5102 | IPARCFDYEI | 241-250 | 6.100 | 445.857770082517 |
| B_5102 | RCFD-YEIEI | 244-252 | 3.000 | 20.0855369231877 |
| B_5102 | FVVR-SKVNI | 282-290 | 3.280 | 26.575772699874 |
| B_5102 | LCF-VRSKV | 280-288 | 3.100 | 22.1979512814416 |
| B_5102 | NIYC-SDDGI | 289-297 | 3.000 | 20.0855369231877 |
| B5102_8mer | NPPQDFEI | 9-16 | 6.200 | 492.749041093256 |
| B5102_8mer | PPQDFEIV | 10-17 | 3.010 | 20.2873999252409 |
| B5102_8mer | DPGYLGYL | 18-25 | 4.610 | 100.484149636389 |
| B5102_8mer | EAKIHTLL | 78-85 | 3.320 | 27.6603505585167 |
| B5102_8mer | WAETTYWI | 99-106 | 4.810 | 122.731617517265 |
| B5102_8mer | YWISPQGI | 104-111 | 3.280 | 26.575772699874 |
| B5102_8mer | QGIPETKV | 109-116 | 5.000 | 148.413159102577 |
| B5102_8mer | KPGIGVLL | 134-141 | 4.710 | 111.052159905699 |
| B5102_8mer | IGCRFPYL | 171-178 | 3.100 | 22.1979512814416 |
| B5102_8mer | FTFQLQNI | 204-211 | 3.890 | 48.9108865237319 |
| B5102_8mer | KPLPPVYL | 213-220 | 5.710 | 301.87106828279 |
| B5102_8mer | IPLGPIPA | 236-243 | 3.610 | 36.9660528148225 |
| B_5103 | NPPQ-DFEIV | 9-17 | 3.800 | 44.7011844933008 |
| B_5103 | IGSETWKTII | 52-61 | 3.900 | 49.4024491055302 |
| B_5103 | DGFD-LNKGI | 69-77 | 3.980 | 53.5170342274912 |
| B_5103 | SPQGIPETKV | 107-116 | 3.800 | 44.7011844933008 |
| B_5103 | EGLDHALQCV | 152-161 | 3.980 | 53.5170342274912 |
| B_5103 | HALQ-CVDYI | 156-164 | 4.890 | 132.953574051283 |
| B_5103 | EASDYKDFYI | 179-188 | 4.610 | 100.484149636389 |
| B_5103 | NGSS-ENKPI | 191-199 | 3.700 | 40.4473043600674 |
| B_5103 | IPARCFDYEI | 241-250 | 3.800 | 44.7011844933008 |
| B_5201 | NPPQ-DFEIV | 9-17 | 4.700 | 109.947172452124 |
| B_5201 | NPPQ-DFEIV | 8-17 | 3.680 | 39.6463940725726 |
| B_5201 | IGSETWKTII | 52-61 | 4.600 | 99.4843156419338 |
| B_5201 | DGFD-LNKGI | 69-77 | 4.110 | 60.9467175696222 |
| B_5201 | FTFQ-LQNIV | 204-212 | 4.600 | 99.4843156419338 |
| B_5801 | KTIITKNLHY | 58-67 | 3.000 | 20.0855369231877 |
| B_5801 | SSWA-ETTYW | 97-105 | 4.390 | 80.640418980477 |
| B_5801 | QSSWAETTYW | 96-105 | 4.390 | 80.640418980477 |
| B_5801 | DTNY-NLFYW | 142-150 | 3.370 | 29.0785270577971 |
| B_5801 | KPLPPVYLTF | 213-222 | 3.100 | 22.1979512814416 |
| B_5801 | SSCE-IKLKW | 226-234 | 5.690 | 295.893620640484 |
| B_5801 | SSCE-IKLKW | 225-234 | 3.800 | 44.7011844933008 |
| B_5801 | TTNETRQLCF | 273-282 | 4.490 | 89.1214458786587 |
| B_5801 | CSDDGIWSEW | 292-301 | 4.900 | 134.289779684936 |
| B_5801 | WSEWSDKQCW | 298-307 | 4.390 | 80.640418980477 |
| B60 | FEIV-DPGYL | 14-22 | 5.770 | 320.537732647356 |
| B60 | VDPG-YLGYL | 17-25 | 3.000 | 20.0855369231877 |
| B60 | KECT-VEYEL | 39-47 | 5.870 | 354.248980267765 |
| B60 | IEAK-IHTLL | 77-85 | 5.870 | 354.248980267765 |
| B60 | RESS-CEIKL | 224-232 | 6.560 | 706.271694595536 |
| B60 | IEIREDDTTL | 250-259 | 5.770 | 320.537732647356 |
| B60 | GEDL-SKKTL | 309-317 | 5.080 | 160.774055928607 |
| B60 | EDLS-KKTLL | 310-318 | 3.690 | 40.0448469572867 |
| B61 | REDDTTLVTA | 253-262 | 3.100 | 22.1979512814416 |
| B61 | NETR-QLCFV | 275-283 | 4.380 | 79.8380334050845 |
| B61_8mer | SEVQSSWA | 93-100 | 3.690 | 40.0448469572867 |
| B61_8mer | REDDTTLV | 253-260 | 3.790 | 44.2564002759834 |
| Cw_0301 | FEIV-DPGYL | 14-22 | 3.000 | 20.0855369231877 |
| Cw_0301 | LYLQ-WQPPL | 25-33 | 3.000 | 20.0855369231877 |
| Cw_0301 | YLYLQWQPPL | 24-33 | 3.000 | 20.0855369231877 |
| Cw_0301 | VEYELKYRNI | 43-52 | 3.630 | 37.7128166171817 |
| Cw_0301 | LHYK-DGFDL | 65-73 | 3.000 | 20.0855369231877 |
| Cw_0301 | KGIEAKIHTL | 75-84 | 3.590 | 36.2340759264765 |
| Cw_0301 | CVYY-NWQYL | 121-129 | 3.360 | 28.7891908792427 |
| Cw_0301 | DCVYYNWQYL | 120-129 | 3.360 | 28.7891908792427 |
| Cw_0301 | VYYN-WQYLL | 122-130 | 3.000 | 20.0855369231877 |
| Cw_0301 | VLLDTNYNLF | 139-148 | 3.400 | 29.964100047397 |
| Cw_0301 | GVLLDTNYNL | 138-147 | 3.000 | 20.0855369231877 |
| Cw_0301 | YNLFYWYEGL | 145-154 | 3.610 | 100.484149636389 |
| Cw_0301 | NLFY-WYEGL | 146-154 | 3.410 | 30.2652442594001 |
| Cw_0301 | QNIGCRFPYL | 169-178 | 3.000 | 100.484149636389 |
| Cw_0301 | KPIRSSYFTF | 197-206 | 3.810 | 45.1504388663187 |
| Cw_0301 | FQLQNIVKPL | 206-215 | 3.180 | 24.0467535520645 |
| Cw_0301 | KPLPPVYLTF | 213-222 | 5.010 | 149.904736149047 |
| Cw_0301 | IKLK-WSIPL | 230-238 | 3.000 | 20.0855369231877 |
| Cw_0301 | ATVENETYTL | 262-271 | 3.590 | 36.2340759264765 |

TABLE I-continued

Binding peptides prediction:

| Allele | Peptide | Position | Score | t½ |
|---|---|---|---|---|
| Cw_0401 | DFEIVDPGYL | 13-22 | 5.300 | 200.336809974792 |
| Cw_0401 | DPGYLGYLYL | 18-27 | 4.390 | 80.640418980477 |
| Cw_0401 | LYLQ-WQPPL | 25-33 | 5.300 | 200.336809974792 |
| Cw_0401 | QPPL-SLDHF | 30-38 | 4.490 | 89.1214458786587 |
| Cw_0401 | HFKE-CTVEY | 37-45 | 3.400 | 29.964100047397 |
| Cw_0401 | EYEL-KYRNI | 44-52 | 3.220 | 25.0281201813378 |
| Cw_0401 | TWKKTIITKNL | 56-65 | 3.690 | 40.0448469572867 |
| Cw_0401 | TYWI-SPQGI | 103-111 | 3.220 | 25.0281201813378 |
| Cw_0401 | IPET-KVQDM | 111-199 | 4.390 | 80.640418980477 |
| Cw_0401 | VYYN-WQYLL | 122-130 | 5.300 | 200.336809974792 |
| Cw_0401 | SWKP-GIGVL | 132-140 | 4.560 | 95.5834798300662 |
| Cw_0401 | WYEG-LDHAL | 150-158 | 5.300 | 200.336809974792 |
| Cw_0401 | WYEG-LDHAL | 149-158 | 3.870 | 47.9423860808193 |
| Cw_0401 | DYIKADGQNI | 162-171 | 3.220 | 25.0281201813378 |
| Cw_0401 | RFPYLEASDY | 174-183 | 3.220 | 25.0281201813378 |
| Cw_0401 | DYKD-FYICV | 182-190 | 3.400 | 29.964100047397 |
| Cw_0401 | KPIRSSYFTF | 197-206 | 3.700 | 40.4473043600674 |
| Cw_0401 | YFTF-QLQNI | 203-211 | 3.910 | 49.8989519734079 |
| Cw_0401 | SYFTFQLQNI | 202-211 | 3.910 | 49.8989519734079 |
| Cw_0401 | KPLPPVYLTF | 213-222 | 3.880 | 48.4242150713452 |
| Cw_0401 | TFTRESSCEI | 221-230 | 3.220 | 25.0281201813378 |
| Cw_0401 | CFVVRSKVNI | 281-290 | 3.220 | 25.0281201813378 |
| Cw_0702 | DPGY-LGYLY | 18-26 | 3.870 | 47.9423860808193 |
| Cw_0702 | DPGY-LGYLY | 17-26 | 3.460 | 31.8169765146677 |

*= high stringency

Example 4

Protein and Nucleic Acid Vaccines Prevent the Development of Tumors

Figure 9:
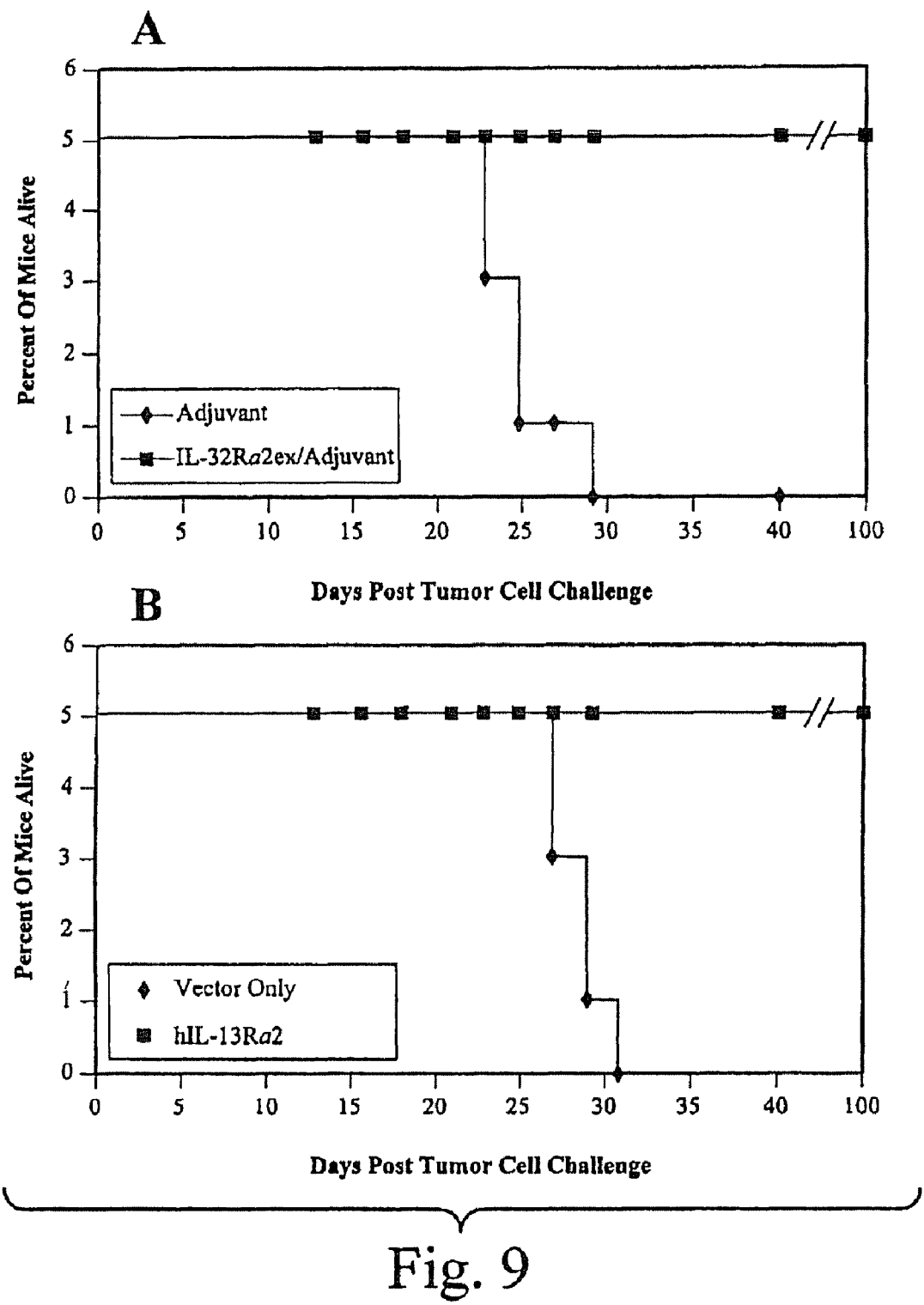
FIG. 9 is two graphs showing the effectiveness of an hIL-13Rα2 recombinant protein vaccine (A) and a nucleic acid vaccine (B) in preventing tumor formation in an animal model.

The effect of an antibody-based immune response against cells expressing IL-13Rα2 was examined. An immunocompetent syngeneic murine glioma model that expresses IL-13Rα2 was established. G-26 murine glioma cells were stably transfected with hIL-13Rα2 and were shown to contain the IL-13 binding characteristics of human HGAs. Furthermore, tumors grown from these IL-13Rα2(+) cells immunocompetent C57BL/J6 mice maintained the HGA restricted IL-13 binding properties, validating this model. Immunocompetent C57BL/J6 mice were injected with affinity-purified extracellular of IL-13Rμ2 recombinant protein domain [6x(His)-(factor X restriction site)-IL-13R α2 (amino acids 27-343)] produced in E. coli. together with Freund's Complete adjuvant or Freund's adjuvant alone (10 male mice per/group, age 10 weeks). Mice were vaccinated every 2 weeks for a total of 3 times. Three weeks after the last vaccination, a substantial load of G-26-hIL-13Rα2(+) tumor cells (5 ×10⁶ cells) were implanted subcutaneously into the vaccinated mice and the controls. Tumors appeared 16 days post tumor cells injection in the control groups but not in the IL-13Rα2 vaccinated group (FIG. 9A). Additionally, mice vaccinated with recombinant IL-13Rα2 manifested a strong specific antibody response against IL-13Rα2 as demonstrated by enzyme-linked immunosorbent assay (ELISA).

Anti-tumor responses by the cell-mediated branch of the immune system were also examined. A plasmid containing IL-13Rα2 under the CMV promoter, pcDNA3.1/IL-13Rα2, or pcDNA3.1 alone was attached to gold particles and used to vaccinate mice via gene gun (10mice/group) (Vaccine 18:2937-2944; 2000). Mice were immunized every two weeks for a total of 3 times. Three weeks after the last immunization, mice were injected subcutaneously with 5 ×10⁶ G-26-IL-13Rα2(+) murine glioma cells. Tumors appeared 16 days after tumor cell injection only in mice vaccinated with pcDNA 3.1 vector alone but no tumors were visible in mice vaccinated with pcDNA 3.1/Rα2 (FIG. 9B).

OTHER EMBODIMENTS

This description has been by way of example of how the compositions and methods of invention can be made and carried out. Those of ordinary skill in the art will recognize that various details may be modified in arriving at the other detailed embodiments, and that many of these embodiments will come within the scope of the invention. Therefore, to apprise the public of the scope of the invention and the embodiments covered by the invention, the following claims are made.

What is claimed is:

1. A method for stimulating an immune response against IL-13Rα2 in a subject having a disease having glioma cells expressing IL-13Rα2, the method comprising the steps of:
   (a) formulating an immunogenic composition outside of the subject having glioma cells expressing IL-13Rα2, the immunogenic composition comprising i) a nucleic acid that encodes a peptide comprising at least seven contiguous amino acids of SEQ ID NO: 1 and ii) an adjuvant;
   (b) administering the immunogenic composition to the subject in an amount sufficient to stimulate an immune response against IL-13Rα2 in the subject; and
   (c) measuring stimulation of an immune response against glioma cells expressing IL-13Rα2 in the subject after administration of the immunogenic composition to the subject.

2. The method of claim 1, wherein the adjuvant comprises a substance selected from the group consisting of: an aluminum salt; an oil-in-water emulsion; a composition comprising saponin; a composition comprising a bacterial protein; and a cytokine.

3. The method of claim 1, wherein step (b) of administering the immunogenic composition to the subject in an amount sufficient to stimulate an immune response against IL-13Rα2 in the subject comprises administering the immunogenic composition in at least a first dose and a second dose, wherein said first dose is administered to the subject at least 24 hours before said second dose is administered to the subject.

4. The method of claim 1, wherein the nucleic acid is a naked DNA.

5. The method of claim 1, wherein the nucleic acid is incorporated into an expression vector.

6. The method of claim 1, further comprising the step of providing a subject having a cancer having cells expressing IL-13Rα2.

7. The method of claim 6, wherein the subject is a human being.

8. The method of claim 1, wherein administering the immunogenic composition to the subject in an amount sufficient to stimulate an immune response against IL-13Rα2 in the subject inhibits tumor growth in vivo, wherein the immunogenic composition comprises the nucleic acid that encodes SEQ ID NO:1.

* * * * *

SEQUENCE LISTING

<160> NUMBER OF SEQ ID NOS: 6

<210> SEQ ID NO 1
<211> LENGTH: 380
<212> TYPE: PRT
<213> ORGANISM: Homo sapiens

<400> SEQUENCE: 1

| Met | Ala | Phe | Val | Cys | Leu | Ala | Ile | Gly | Cys | Leu | Tyr | Thr | Phe | Leu | Ile |
|---|---|---|---|---|---|---|---|---|---|---|---|---|---|---|---|
| 1 | | | | 5 | | | | | 10 | | | | | 15 | |

| Ser | Thr | Thr | Phe | Gly | Cys | Thr | Ser | Ser | Asp | Thr | Glu | Ile | Lys | Val |
|---|---|---|---|---|---|---|---|---|---|---|---|---|---|---|
| | | | 20 | | | | | 25 | | | | | 30 | |

| Asn | Pro | Pro | Gln | Asp | Phe | Glu | Ile | Val | Asp | Pro | Gly | Tyr | Leu | Gly | Tyr |
|---|---|---|---|---|---|---|---|---|---|---|---|---|---|---|---|
| | | 35 | | | | | 40 | | | | | 45 | | | |

| Leu | Tyr | Leu | Gln | Trp | Gln | Pro | Pro | Leu | Ser | Leu | Asp | His | Phe | Lys | Glu |
|---|---|---|---|---|---|---|---|---|---|---|---|---|---|---|---|
| | 50 | | | | | 55 | | | | | 60 | | | | |

| Cys | Thr | Val | Glu | Tyr | Glu | Leu | Lys | Tyr | Arg | Asn | Ile | Gly | Ser | Glu | Thr |
|---|---|---|---|---|---|---|---|---|---|---|---|---|---|---|---|
| 65 | | | | 70 | | | | | 75 | | | | | 80 | |

| Trp | Lys | Thr | Ile | Ile | Thr | Lys | Asn | Leu | His | Tyr | Lys | Asp | Gly | Phe | Asp |
|---|---|---|---|---|---|---|---|---|---|---|---|---|---|---|---|
| | | | | 85 | | | | | 90 | | | | | 95 | |

| Leu | Asn | Lys | Gly | Ile | Glu | Ala | Lys | Ile | His | Thr | Leu | Leu | Pro | Trp | Gln |
|---|---|---|---|---|---|---|---|---|---|---|---|---|---|---|---|
| | | | 100 | | | | | 105 | | | | | 110 | | |

| Cys | Thr | Asn | Gly | Ser | Glu | Val | Gln | Ser | Ser | Trp | Ala | Glu | Thr | Thr | Tyr |
|---|---|---|---|---|---|---|---|---|---|---|---|---|---|---|---|
| | | | | 115 | | | | | 120 | | | | | 125 | |

| Trp | Ile | Ser | Pro | Gln | Gly | Ile | Pro | Glu | Thr | Lys | Val | Gln | Asp | Met | Asp |
|---|---|---|---|---|---|---|---|---|---|---|---|---|---|---|---|
| | 130 | | | | | 135 | | | | | 140 | | | | |

| Cys | Val | Tyr | Tyr | Asn | Trp | Gln | Tyr | Leu | Leu | Cys | Ser | Trp | Lys | Pro | Gly |
|---|---|---|---|---|---|---|---|---|---|---|---|---|---|---|---|
| 145 | | | | | 150 | | | | | 155 | | | | | 160 |

| Ile | Gly | Val | Leu | Leu | Asp | Thr | Asn | Tyr | Asn | Leu | Phe | Tyr | Trp | Tyr | Glu |
|---|---|---|---|---|---|---|---|---|---|---|---|---|---|---|---|
| | | | | 165 | | | | | 170 | | | | | 175 | |

| Gly | Leu | Asp | His | Ala | Leu | Gln | Cys | Val | Asp | Tyr | Ile | Lys | Ala | Asp | Gly |
|---|---|---|---|---|---|---|---|---|---|---|---|---|---|---|---|
| | | | 180 | | | | | 185 | | | | | 190 | | |

| Gln | Asn | Ile | Gly | Cys | Arg | Phe | Pro | Tyr | Leu | Glu | Ala | Ser | Asp | Tyr | Lys |
|---|---|---|---|---|---|---|---|---|---|---|---|---|---|---|---|
| | | 195 | | | | | 200 | | | | | 205 | | | |

| Asp | Phe | Tyr | Ile | Cys | Val | Asn | Gly | Ser | Ser | Glu | Asn | Lys | Pro | Ile | Arg |
|---|---|---|---|---|---|---|---|---|---|---|---|---|---|---|---|
| | 210 | | | | | 215 | | | | | 220 | | | | |

| Ser | Ser | Tyr | Phe | Thr | Phe | Gln | Leu | Gln | Asn | Ile | Val | Lys | Pro | Leu | Pro |
|---|---|---|---|---|---|---|---|---|---|---|---|---|---|---|---|
| 225 | | | | | 230 | | | | | 235 | | | | | 240 |

| Pro | Val | Tyr | Leu | Thr | Phe | Thr | Arg | Glu | Ser | Ser | Cys | Glu | Ile | Lys | Leu |
|---|---|---|---|---|---|---|---|---|---|---|---|---|---|---|---|
| | | | | 245 | | | | | 250 | | | | | 255 | |

| Lys | Trp | Ser | Ile | Pro | Leu | Gly | Pro | Ile | Pro | Ala | Arg | Cys | Phe | Asp | Tyr |
|---|---|---|---|---|---|---|---|---|---|---|---|---|---|---|---|
| | | | 260 | | | | | 265 | | | | | 270 | | |

| Glu | Ile | Glu | Ile | Arg | Glu | Asp | Asp | Thr | Thr | Leu | Val | Thr | Ala | Thr | Val |
|---|---|---|---|---|---|---|---|---|---|---|---|---|---|---|---|
| | | | 275 | | | | | 280 | | | | | 285 | | |

| Glu | Asn | Glu | Thr | Tyr | Thr | Leu | Lys | Thr | Thr | Asn | Glu | Thr | Arg | Gln | Leu |
|---|---|---|---|---|---|---|---|---|---|---|---|---|---|---|---|
| | | 290 | | | | | 295 | | | | | 300 | | | |

| Cys | Phe | Val | Val | Arg | Ser | Lys | Val | Asn | Ile | Tyr | Cys | Ser | Asp | Asp | Gly |
|---|---|---|---|---|---|---|---|---|---|---|---|---|---|---|---|
| 305 | | | | | 310 | | | | | 315 | | | | | 320 |

| Ile | Trp | Ser | Glu | Trp | Ser | Asp | Lys | Gln | Cys | Trp | Glu | Gly | Glu | Asp | Leu |
|---|---|---|---|---|---|---|---|---|---|---|---|---|---|---|---|
| | | | | 325 | | | | | 330 | | | | | 335 | |

| Ser | Lys | Lys | Thr | Leu | Leu | Arg | Phe | Trp | Leu | Pro | Phe | Gly | Phe | Ile | Leu |
|---|---|---|---|---|---|---|---|---|---|---|---|---|---|---|---|
| | | | 340 | | | | | 345 | | | | | 350 | | |

| Ile | Leu | Val | Ile | Phe | Val | Thr | Gly | Leu | Leu | Leu | Arg | Lys | Pro | Asn | Thr |
|---|---|---|---|---|---|---|---|---|---|---|---|---|---|---|---|
| | | | 355 | | | | | 360 | | | | | 365 | | |

| Tyr | Pro | Lys | Met | Ile | Pro | Glu | Phe | Phe | Cys | Asp | Thr |
|---|---|---|---|---|---|---|---|---|---|---|---|
| | 370 | | | | | 375 | | | | | 380 |

<210> SEQ ID NO 2
<211> LENGTH: 1298
<212> TYPE: DNA
<213> ORGANISM: Homo sapiens

```
<400> SEQUENCE: 2
ggtgcctgtc ggcggggaga gaggcaatat caaggtttta aatctcggag aaatggcttt      60
cgtttgcttg gctatcggat gcttatatac ctttctgata agcacaacat ttggctgtac     120
ttcatcttca gacaccgaga taaaagttaa ccctcctcag gattttgaga tagtggatcc     180
cggatactta ggttatctct atttgcaatg gcaaccccca ctgtctctgg atcattttaa     240
ggaatgcaca gtggaatatg aactaaaata ccgaaacatt ggtagtgaaa catggaagac     300
catcattact aagaatctac attacaaaga tgggtttgat cttaacaagg cattgaagc      360 gaagatacac acgcttttac catggcaatg cacaaatgga tcagaagttc aaagttcctg     420
ggcagaaact acttattgga tatcaccaca aggaattcca gaaactaaag ttcaggatat     480
ggattgcgta tattacaatt ggcaatattt actctgttct tggaaacctg gcataggtgt     540
acttcttgat accaattaca acttgtttta ctggtatgag ggcttggatc atgcattaca     600
gtgtgttgat tacatcaagg ctgatggaca aaatatagga tgcagatttc cctatttgga     660
ggcatcagac tataaagatt tctatatttg tgttaatgga tcatcagaga caagcctat      720 cagatccagt tatttcactt ttcagcttca aaatatagtt aaacctttgc cgccagtcta     780
tcttactttt actcgggaga gttcatgtga aattaagctg aaatggagca tacctttggg     840
acctattcca gcaaggtgtt ttgattatga aattgagatc agagaagatg atactacctt     900
ggtgactgct acagttgaaa atgaaacata caccttgaaa acaacaaatg aaacccgaca     960
attatgcttt gtagtaagaa gcaaagtgaa tatttattgc tcagatgacg gaatttggag    1020
tgagtggagt gataaacaat gctgggaagg tgaagaccta tcgaagaaaa ctttgctacg    1080
tttctggcta ccatttggtt tcatcttaat attagttata tttgtaaccg gtctgctttt    1140
gcgtaagcca aacacctacc caaaaatgat tccagaattt ttctgtgata catgaagact    1200
ttccatatca agagacatgg tattgactca acagtttcca gtcatggcca aatgttcaat    1260
atgagtctca ataaactgaa tttttcttgc gaatgttg                            1298

<210> SEQ ID NO 3
<211> LENGTH: 30
<212> TYPE: DNA
<213> ORGANISM: Artificial Sequence
<220> FEATURE:
<221> NAME/KEY: misc_feature
<223> OTHER INFORMATION: Forward PCR Primer for IL-13Ralpha2

<400> SEQUENCE: 3
aagatttgga agcttatggc tttcgtttgc                                       30

<210> SEQ ID NO 4
<211> LENGTH: 30
<212> TYPE: DNA
<213> ORGANISM: Artificial Sequence
<220> FEATURE:
<221> NAME/KEY: misc_feature
<223> OTHER INFORMATION: Reverse PCR Primer for IL-13Ralpha2

<400> SEQUENCE: 4
tccctcgaag cttcatgtat cacagaaaaa                                       30

<210> SEQ ID NO 5
<211> LENGTH: 27
<212> TYPE: DNA
<213> ORGANISM: Artificial Sequence
<220> FEATURE:
<221> NAME/KEY: misc_feature
<223> OTHER INFORMATION: Forward PCR Primer for IL-13Ralpha1
```

```
-continued

<400> SEQUENCE: 5
attattaagc ttatggagtg gccggcg                                             27

<210> SEQ ID NO 6
<211> LENGTH: 27
<212> TYPE: DNA
<213> ORGANISM: Artficial Sequence
<220> FEATURE:
<221> NAME/KEY: misc_feature
<223> OTHER INFORMATION: Reverse PCR Primer For IL-13Ralpha1

<400> SEQUENCE: 6
taaccggaag cttcactgag aggcttt                                             27
```